US012642476B1

(12) United States Patent
Franceschi

(10) Patent No.: US 12,642,476 B1
(45) Date of Patent: Jun. 2, 2026

(54) MONITORING DIAPHRAGMATIC ELECTRICAL ACTIVITY

(71) Applicant: Circle Safe, Aubagne (FR)

(72) Inventor: Frédéric Franceschi, Aubagne (FR)

(73) Assignee: Circle Safe, Aubagne (FR)

( * ) Notice: Subject to any disclaimer, the term of this patent is extended or adjusted under 35 U.S.C. 154(b) by 0 days.

(21) Appl. No.: 19/047,997

(22) Filed: Feb. 7, 2025

(30) Foreign Application Priority Data

Feb. 3, 2025 (EP) ..................................... 25305153

(51) Int. Cl.
A61B 18/18 (2006.01)
A61B 5/00 (2006.01)
(Continued)

(52) U.S. Cl.
CPC .............. A61B 5/395 (2021.01); A61B 5/294 (2021.01); A61B 5/6852 (2013.01);
(Continued)

(58) Field of Classification Search
CPC .......... A61B 2562/063; A61B 5/02438; A61B 5/113; A61B 5/349; A61B 5/352;
(Continued)

(56) References Cited

U.S. PATENT DOCUMENTS

RE30,366 E    8/1980   Rasor et al.
4,574,807 A   3/1986   Hewson et al.
(Continued)

FOREIGN PATENT DOCUMENTS

EP    0010908 B1   10/1979
EP    1572293 B1   10/2003
(Continued)

OTHER PUBLICATIONS

Anwar, O. et al., "Contemporary analysis of phrenic nerve injuries following cryoballoon-based pulmonary vein isolation: A single-centre experience with the systematic use of compound motor action potential monitoring," PLoS One, vol. 15, Issue 6, Jun. 25, 2020, 11 pages.

(Continued)

*Primary Examiner* — Michael F Peffley
*Assistant Examiner* — Amanda L Zink
(74) *Attorney, Agent, or Firm* — Alleman Hall LLP

(57) ABSTRACT

The disclosure notably relates to an apparatus for minimally invasive medical use, comprising an elongated part including a catheter and/or a catheter sheath, the elongated part having a distal portion and an intermediate portion, the elongated part being configured for being introduced inside the inferior vena cava of a human patient and positioned at an operating location where the distal portion is in and/or beyond the right atrium and the intermediate portion is in the inferior vena cava, and one or more monitoring electrodes arranged on the intermediate portion of the elongated part, the one or more monitoring electrodes being configured for monitoring an electrical activity of the diaphragm of the human patient when the elongated part is positioned at the operating location. This forms an improved solution for monitoring an electrical activity of the diaphragm of a human patient.

15 Claims, 8 Drawing Sheets

(51) Int. Cl.

| | | |
|---|---|---|
| *A61B 5/294* | (2021.01) | |
| *A61B 5/395* | (2021.01) | |
| *A61B 18/14* | (2006.01) | |
| *A61B 18/00* | (2006.01) | |

(52) U.S. Cl.
CPC ..... *A61B 18/1492* (2013.01); *A61B 2018/00357* (2013.01); *A61B 2018/00577* (2013.01)

(58) Field of Classification Search
CPC ..... A61B 5/4836; A61B 5/686; A61B 5/6867; A61B 5/721; A61B 5/7246
See application file for complete search history.

(56) References Cited

U.S. PATENT DOCUMENTS

| | | | |
|---|---|---|---|
| 4,683,890 | A | 8/1987 | Hewson |
| 5,052,390 | A | 10/1991 | Hewson |
| 7,340,302 | B1 | 3/2008 | Falkenberg et al. |
| 7,894,915 | B1 | 2/2011 | Chitre et al. |
| 8,412,350 | B2 | 4/2013 | Bly |
| 8,456,182 | B2 | 6/2013 | Bar-Tal et al. |
| 8,706,235 | B2 | 4/2014 | Karamanoglu et al. |
| 8,897,879 | B2 | 11/2014 | Karamanoglu et al. |
| 9,050,453 | B2 | 6/2015 | Inagaki et al. |
| 9,168,377 | B2 | 10/2015 | Hoffer |
| 9,333,363 | B2 | 5/2016 | Hoffer et al. |
| 9,415,225 | B2 | 8/2016 | Shuros et al. |
| 10,064,564 | B2 | 9/2018 | Kowalski et al. |
| 10,507,322 | B2 | 12/2019 | Westlund et al. |
| 10,512,772 | B2 | 12/2019 | Hoffer et al. |
| 11,553,963 | B2 | 1/2023 | Franceschi et al. |
| 11,759,141 | B2 | 9/2023 | Franceschi et al. |
| 12,295,652 | B2 * | 5/2025 | Zemlin ............ A61B 18/1492 |
| 2002/0165532 | A1 | 11/2002 | Hill, III et al. |
| 2005/0197675 | A1 | 9/2005 | David et al. |
| 2006/0282124 | A1 | 12/2006 | Diaz et al. |
| 2008/0009846 | A1 | 1/2008 | Ward |
| 2008/0281312 | A1 | 11/2008 | Werneth et al. |
| 2010/0079158 | A1 | 4/2010 | Bar-Tal et al. |
| 2013/0030496 | A1 | 1/2013 | Karamanoglu et al. |
| 2013/0109994 | A1 * | 5/2013 | Cho ..................... A61B 5/1104 |
| | | | 606/1 |
| 2013/0296840 | A1 | 11/2013 | Condie et al. |
| 2014/0358135 | A1 | 12/2014 | Sambelashvili et al. |
| 2015/0057563 | A1 * | 2/2015 | Kowalski .............. A61B 5/389 |
| | | | 600/554 |
| 2015/0141798 | A1 | 5/2015 | Bar-Tal |
| 2015/0265833 | A1 | 9/2015 | Meyyappan et al. |
| 2016/0220822 | A1 | 8/2016 | Hoffer et al. |
| 2017/0189106 | A1 | 7/2017 | Schuler et al. |
| 2018/0344244 | A1 | 12/2018 | Botzer et al. |
| 2020/0077938 | A1 | 3/2020 | Jung et al. |
| 2022/0287768 | A1 | 9/2022 | Franceschi et al. |
| 2023/0026175 | A1 * | 1/2023 | Franceschi ............. A61B 5/395 |
| 2024/0173074 | A1 | 5/2024 | Franceschi et al. |
| 2024/0350192 | A1 * | 10/2024 | Sharma .............. A61B 18/1492 |
| 2025/0049490 | A1 * | 2/2025 | Schuler .................. A61B 18/02 |

FOREIGN PATENT DOCUMENTS

| | | | |
|---|---|---|---|
| EP | 1802370 | B1 | 5/2005 |
| EP | 2371416 | B1 | 11/2006 |
| EP | 3119275 | B1 | 3/2015 |
| EP | 4056135 | A1 | 3/2021 |
| WO | 2018212840 | A1 | 11/2018 |
| WO | 2019126281 | A1 | 6/2019 |

OTHER PUBLICATIONS

Arai, T. et al., "A new method of superior vena cava isolation without phrenic nerve injury by longitudinal ablation parallel to the phrenic nerve: a case report," European Heart Journal—Case Reports, vol. 4, Issue 5, Sep. 9, 2020, 4 pages.

Augostini, R. S. et al., "How to implant a phrenic nerve stimulator for treatment of central sleep apnea?," Journal of Cardiovascular Electrophysiology, vol. 30, Issue 5, Mar. 4, 2019, 8 pages.

Chikata, A. et al., "Coronary sinus catheter placement via left cubital vein for phrenic nerve stimulation during pulmonary vein isolation," Heart and Vessels, vol. 34, Apr. 10, 2019, 7 pages.

Dimarco, A. F. et al., "Combined Intercostal and Diaphragm Pacing to Provide Artificial Ventilation in Patients With Tetraplegia," Archives of Physical Medicine and Rehabilitation, vol. 86, Issue 6, Jun. 2005, 8 pages.

European Patent Office, Extended European Search Report Issued in Application No. 21306024.7, Jan. 7, 2022, 11 pages.

European Patent Office, Extended European Search Report Issued in Application No. 25305153.6, Apr. 9, 2025, 10 pages.

European Patent Office, Extended European Search Report Issued in Application No. 21305287.1, Sep. 6, 2021, 7 pages.

Franceschi, F. et al., "Diaphragmatic electromyography during cryoballoon ablation: a novel concept in the prevention of phrenic nerve palsy," Heart Rhythm, vol. 8, No. 6, Jun. 2011, 7 pages.

Franceschi, F. et al., "Electromyographic Monitoring for Prevention of Phrenic Nerve Palsy in Second-Generation Cryoballoon Procedures," Circulation: Arrhythmia and Electrophysiology, vol. 8, No. 2, Mar. 4, 2015, 6 pages.

Franceschi, F. et al., "Novel Electromyographic Monitoring Technique for Prevention of Right Phrenic Nerve Palsy During Cryoballoon Ablation," Circulation: Arrhythmia and Electrophysiology, vol. 6, No. 6, Oct. 10, 2023, 7 pages.

Franceschi, F. et al., "Phrenic nerve monitoring with diaphragmatic electromyography during cryoballoon ablation for atrial fibrillation: The first human application," Heart Rhythm, vol. 8, No. 7, Jul. 2011, 4 pages.

ISA European Patent Office, International Search Report and Written Opinion Issued in Application No. PCT/EP2022/070278, Nov. 18, 2022, WIPO, 19 pages.

ISA European Patent Office, International Search Report and Written Opinion Issued in Application No. PCT/EP2022/055952, Jun. 8, 2022, WIPO, 16 pages.

Kaczmarek, K. et al., "Straight and crosier-shaped catheter techniques for phrenic nerve stimulation during cryoballoon pulmonary vein isolation for the treatment of atrial fibrillation," Kardiologia Polska, vol. 77, Issue 9, Jul. 22, 2019, 7 pages.

Luo, Y. M. et al., "Quantification of the Esophageal Diaphragm Electromyogram with Magnetic Phrenic Nerve Stimulation," American Journal of Respiratory and Critical Care Medicine, vol. 160, Nov. 1999, 6 pages.

Okishige, K. et al., "Novel method for earlier detection of phrenic nerve injury during cryoballoon applications for electrical isolation of pulmonary veins in patients with atrial fibrillation," Heart Rhythm, vol. 13, No. 9, Sep. 2016, 7 pages.

Reynolds, S. et al., "Diaphragm Activation in Ventilated Patients Using a Novel Transvenous Phrenic Nerve Pacing Catheter," Critical Care Medicine, vol. 45, Issue 7, Jul. 2017, 4 pages.

Sharma, P. S. et al., "Factors Influencing Diaphragmatic Compound Motor Action Potentials During Cryoballoon Ablation for Atrial Fibrillation," Journal of Cardiovascular Electrophysiology, vol. 27, No. 12, Dec. 2016, 6 pages.

Tovmassian, L. et al., "Diaphragmatic CMAP Monitoring During Cryoballoon Procedures: Surface vs. Hepatic Recording Comparison and Limitations of This Approach," Frontiers in Cardiovascular Medicine, vol. 9, Feb. 7, 2022, 7 pages.

Miyazaki, S. et al., "Evaluation of Diaphragmatic Electromyograms in Radiofrequency Ablation of Atrial Fibrillation: Prospective Study Comparing Different Monitoring Techniques," Journal of Cardiovascular Electrophysiology, vol. 26, No. 3, Oct. 27, 2014, 6 pages.

"Blazer DX-20 Bidirectional Duodecapolar Diagnostic Catheter," Boston Scientific, Available Online at https://web.archive.org/web/20250114053108/https://www.bostonscientific.com/en-US/products/catheters--diagnost, Available as Early as Jan. 14, 2025, 4 pages.

"Atrial Cardioversion System BeeAT / Shock AT," Japan Lifeline, Available Online at https://web.archive.org/web/20241110025114/https://product.japanlifeline.com/ep/products/cardioversion/beeat/, Available as Early as Mar. 2, 2024, 9 pages.

(56)  References Cited

OTHER PUBLICATIONS

European Patent Office, Communication pursuant to Article 94(3) EPC Issued in Application No. 25305153.6, Feb. 27, 2026, Germany, 8 pages.

* cited by examiner

SVC

PN

H

10

I

252

256

250

MONITORING DIAPHRAGMATIC ELECTRICAL ACTIVITY

TECHNICAL FIELD

The present disclosure relates to minimally invasive medical procedures and devices for such use, and in particular to apparatuses, units, computer programs, kits, and methods for monitoring an electrical activity of the diaphragm of the human patient, for example during phrenic nerve stimulation, such as within an ablation procedure.

BACKGROUND

Monitoring the electrical activity of the diaphragm of a human patient may serve a number of purposes. Notably, monitoring the electrical activity of the diaphragm may enable evaluating the correct functioning of the right phrenic nerve of the patient, and thereby detecting a (current or upcoming) dysfunction or malfunction of said right phrenic nerve. Such dysfunction or malfunction may have a number of causes, and for example be the result of an impact on the right phrenic nerve of a treatment that the patient is undergoing or has undergone. For instance, the patient may be subjected to a cardiac treatment procedure presenting risks of (temporarily or permanently) injuring the right phrenic nerve. A manner to prevent or reduce risks of such injury may comprise stimulating (or "pacing") the right phrenic nerve of the patient during the cardiac treatment procedure, and observing the diaphragmatic response to detect any current or upcoming dysfunction or malfunction of the right phrenic nerve. The medical practitioner or team may then interrupt (stop or pause) the cardiac treatment procedure, upon such detection.

An example of such cardiac treatment procedure is the ablation of atrial fibrillation with a minimally invasive procedure. Atrial fibrillation is a common arrhythmia condition. Atrial fibrillation ablation is a type of cardiac ablation, which works by scarring or destroying tissue in the heart to disrupt faulty electrical signals causing the arrhythmia. For example, one or both pulmonary veins may be isolated by creating a circumferential lesion, e.g., surrounding their ostia.

Among minimally invasive cardiac ablation techniques, cardiac cryoablation is a procedure very popular within the community of electrophysiology practitioners. Cryoablation techniques consist in electrical isolation of the pulmonary veins of the heart by cold "burning" of the tissues with a cryoablation catheter, most often a cryoballoon catheter (i.e., cryogenic balloon catheter).

The most common complication of cryoablation techniques is right diaphragmatic palsy caused by injury of the right phrenic nerve, due to the close proximity between the right phrenic nerve and the pulmonary veins. Although such injury does not systematically occur during cryoablation procedures, it still affects a non-negligible number of patients. And even though the injury is most often reversible, a relatively significant part of the concerned patients are still affected on the next day, and for some patients the diaphragmatic palsy may last over a relatively long period of time before self-cure.

The research article "Contemporary analysis of phrenic nerve injuries following cryoballoon-based pulmonary vein isolation: A single-centre experience with the systematic use of compound motor action potential monitoring", Anwar, O. et. al., 2020, provides an overview of injury of the right phrenic nerve due to cryoablation, as well as techniques for reducing such injury and issues related to such techniques. One technique widely spread and reviewed in this paper is to perform an electric stimulation of the right phrenic nerve during the cryoablation procedure. As the phrenic nerve controls muscle contraction of the right diaphragmatic dome, the technique further comprises monitoring the contraction response induced by the electrical stimulation and acting thereupon.

Other atrial fibrillation ablation techniques may also cause the same complication of right phrenic nerve injury and right diaphragmatic palsy. This is notably the case of radiofrequency ablation and electroporation (also known as "Pulsed Field Ablation"). Such other techniques may thus similarly benefit from right phrenic nerve stimulation and diaphragmatic monitoring. In particular, pulsed Field Ablation (PFA) is a technique currently gaining popularity, and which uses a series of high amplitude electrical pulses of microsecond-order duration to cause electrical isolation of the pulmonary veins of the heart. Typically, there are eight or more applications (in series) per each pulmonary vein, each application lasting a few milliseconds. As for cryoablation, due to the close vicinity between the right phrenic nerve and the pulmonary veins, the most common complication of PFA is right phrenic nerve palsy.

FIG. 1 illustrates the conventional manner in the prior art to perform phrenic nerve stimulation. The figure shows an example of an anatomical section H of the heart on the left side and a corresponding medical image I on the right side, exemplifying the positioning of an electrophysiology catheter 10 for electrical stimulation of the right phrenic nerve PN. Stimulation catheter 10 is introduced through the femoral vein and positioned with its distal end 14 inside the superior vena cava SVC to stimulate the phrenic nerve PN. Stimulation catheter 10 comprises at its distal end 14 several (e.g., four) electrodes 11 which are positioned inside the superior vena cava (above the heart), to be as close as possible and facing the phrenic nerve PN. Stimulation catheter 10 may be a straight quadripolar catheter, a commercially available catheter commonly used. The operator places the electrodes 11 to stimulate the phrenic nerve by operating in a bipolar mode two electrodes. The operator observes the diaphragmatic contraction caused by the electrical stimulation, which helps the operator to make assessments on possible injury of the right phrenic nerve. Such assessments allow the operator to make clinical decisions to reduce possibilities of complications.

U.S. patent application Ser. No. 18/549,733, corresponding to publication WO 2022/189465 A1 (entitled "Phrenic Nerve Stimulation" and filed in the name of Circle Safe) and the content of which is incorporated herein by reference, discloses systems, catheters, kits, and methods also for performing right phrenic nerve stimulation, but in an improved manner, and for performing a cardiac cryoablation procedure which includes the right phrenic nerve stimulation and the monitoring of a diaphragmatic response to said phrenic nerve stimulation.

Current solutions to assess the muscular response to the phrenic nerve stimulation are mostly based on abdominal palpation by an operator (e.g. a medical professional). When the operator perceives a decrease of the vigor of the diaphragmatic contraction, or when the contraction vanishes, it means that the phrenic nerve has been injured, and the cryoablation is interrupted in emergency. These solutions are thus subjective and relatively inaccurate. Furthermore, they do not allow to avoid right diaphragmatic palsy, but rather establish a diagnostic that a palsy has occurred.

Other solutions include monitoring by a dedicated system a diaphragmatic compound motor action potential (CMAP) signal of the human patient in response to the phrenic nerve stimulation. The CMAP signal is an electrical signal captured by one or more monitoring electrodes, and which contains patterns each representing a (e.g., right) diaphragmatic response to a phrenic nerve stimulation signal (received by the—e.g., right-phrenic nerve), i.e., an electrical current generated in order to stimulate the phrenic nerve so as to obtain a contraction of the diaphragm. The patterns may each be shaped as a wave and be referred to as "a CMAP" or "CMAP pattern". This allows performing objective analysis of the signal and reacting to unusual situations.

U.S. patent application Ser. No. 18/290,748, corresponding to publication WO 2023/001859 A1 (entitled "Monitoring Diaphragmatic Response To Phrenic Nerve Stimulation" and filed in the name of Circle Safe) and the content of which is incorporated herein by reference, discloses methods, programs, control units, apparatuses and systems, for implementing such a solution of diaphragmatic monitoring based on a diaphragmatic CMAP signal.

However, there is still room for an improved solution for monitoring an electrical activity of the diaphragm of a human patient, notably during phrenic nerve stimulation, in particular right phrenic nerve stimulation within an ablation procedure.

SUMMARY

It is therefore provided an apparatus for minimally invasive medical use. The apparatus comprises an elongated part. The elongated part includes a catheter and/or a catheter sheath. The apparatus further comprises one or more monitoring electrodes arranged on the elongated part and configured for monitoring an electrical activity of the diaphragm of the human patient (at least) when the one or more monitoring electrodes are positioned in the inferior vena cava. The elongated part is configured for being introduced inside the inferior vena cava of a human patient and positioned at an operating location where the one or more monitoring electrodes are in the inferior vena cava.

In a first embodiment, the elongated part has a distal portion and an intermediate portion, and the one or more monitoring electrodes are arranged on the intermediate portion of the elongated part. When the elongated part is introduced inside the inferior vena cava of the human patient and positioned at the operating location, the distal portion is in and/or beyond the right atrium and the intermediate portion is in the inferior vena cava, the one or more monitoring electrodes thereby also being positioned in the inferior vena cava.

In a second embodiment, the elongated part has a distal portion, and the one or more monitoring electrodes are arranged on the distal portion of the elongated part. When the elongated part is introduced inside the inferior vena cava of the human patient and positioned at the operating location, the distal portion is the inferior vena cava, the one or more monitoring electrodes thereby also being positioned in the inferior vena cava. In the second embodiment, the distal portion may optionally comprise a distal end of the elongated part, and when the elongated part is introduced inside the inferior vena cava of the human patient and positioned at the operating location, the distal end is positioned in the inferior vena cava.

In examples of all embodiments, the apparatus may present any one or any combination of the following optional features:

the one or more monitoring electrodes comprise at least one monitoring electrode arranged on an external surface of the elongated part (of the intermediate portion or distal portion thereof);

the elongated part includes the catheter sheath, and the one or more monitoring electrodes comprise at least one monitoring electrode arranged on the catheter sheath;

the elongated part includes the catheter, the catheter is a sheath-less catheter or a withdrawable-sheath catheter, the catheter has a shaft, and the one or more monitoring electrodes comprise at least one monitoring electrode arranged on the shaft;

the one or more monitoring electrodes comprise at least two electrodes arranged at different longitudinal positions of the intermediate portion;

the at least two electrodes comprise a first electrode at a distance from a second electrode higher than or equal to 1 cm and/or lower than or equal to 20 cm, for example between 5 cm and 10 cm; and/or the one or more monitoring electrodes comprises at least two individual electrodes (e.g., the at least two electrodes) configured to form a dipole.

In examples of the first embodiment, the apparatus may present any one or any combination of the following optional features:

the elongated part includes the catheter, the distal portion includes an extremal portion of the catheter, and the extremal portion comprises an energy measurement and/or delivery tool;

the energy measurement and/or delivery tool comprises one or more electrodes, one or more probes, and/or one or more cryotherapy delivery tools, such as a cryoballoon;

the energy measurement and/or delivery tool comprises one or more stimulation electrodes, the catheter being configured to be introduced in the superior vena cava of the human patient so as to position the one or more stimulation electrodes in the superior vena cava, in the right brachiocephalic vein, and/or in the right subclavian vein, the one or more stimulation electrodes being configured for stimulation of the right phrenic nerve;

the elongated part has a distal end, and the one or more monitoring electrodes comprise at least one electrode arranged, when the elongated part is positioned at the operating location, at a distance from the distal end higher than or equal to 10 cm and/or lower than or equal to 40 cm, for example between 20 cm and 30 cm; and/or the elongated part includes the catheter, and the catheter is a stimulation catheter configured for phrenic nerve stimulation and that presents all or a combination of the features of any one of the stimulation catheters described in U.S. patent application Ser. No. 18/549, 733, corresponding to publication WO 2022/189465 A1, the distal portion thereby having arranged thereon one or more intravascular stimulation electrodes configured to be operated in a bipolar mode with an extracorporeal electrode patch which is configured to be affixed to the patient opposite to the distal portion relative to the phrenic nerve, so as to perform phrenic nerve stimulation; optionally, the catheter may present the additional or alternative feature that the one or more intravascular stimulation electrodes are configured to be operated so as to form one or more pairs, each pair containing a first group of one or more intravascular stimulation electrodes and a second group of one or more intravascular stimulation electrodes, where the two groups of each pair are operated in a bipolar mode (as illustrated by the prior art example of FIG. 1), so as to perform phrenic nerve stimulation, and/or (additionally or alternatively) the one or more intravascular stimulation electrodes are configured to be operated in a bipolar mode with another type of extracorporeal electrode (different from the extracorporeal electrode patch), so as to perform phrenic nerve stimulation.

It is further provided a unit for monitoring an electrical activity of the diaphragm of a human patient. The monitoring unit is configured for receiving and processing an electrical signal captured by one or more monitoring electrodes positioned intravascularly, such as in the inferior vena cava, so as to monitor the electrical activity of the diaphragm of the human patient at such positioning. The monitoring unit may comprise one or more processors and a memory having recorded thereon a computer program, so as to provide such configuration. Optionally, the monitoring unit may be configured for being electrically connected to the one or more monitoring electrodes.

In examples, the monitoring unit may present any one or any combination of the following optional features:

the monitoring unit is configured to be coupled to (e.g., electrically connected to) and used in conjunction with the above-described apparatus, and the one or more monitoring electrodes from which the monitoring unit receives an electrical signal are those arranged on the elongated part of the apparatus;

when (i) the apparatus is structured according to the first embodiment and (ii) the one or more monitoring electrodes are those arranged on the intermediate portion of the elongated part of the apparatus, (iii) the elongated part of the apparatus includes the catheter, (iv) the distal portion of the elongated part includes an extremal portion of the catheter, and (v) the extremal portion comprises an energy measurement and/or delivery tool, then, the monitoring unit is further configured for being coupled to the energy measurement and/or delivery tool and for controlling (i.e., commanding operation of) the energy measurement and/or delivery tool, for example so as to command right phrenic nerve stimulation or so as to perform (e.g., atrial fibrillation) ablation (such a cryoablation or electroporation);

the monitoring unit is further configured for commanding phrenic nerve stimulation or for being used in conjunction with a control unit that commands phrenic nerve stimulation, and the monitoring of the electrical activity of the diaphragm of the human patient is performed as a function of a timing of the phrenic nerve stimulation (e.g., as a function of the time at which each phrenic nerve stimulation occurrence starts);

the phrenic nerve stimulation comprises occurrences of phrenic nerve stimulation, each occurrence of phrenic nerve stimulation corresponding to a single stimulation signal sent to the (e.g., right) phrenic nerve, and the monitoring unit is configured for identifying a start of each respective occurrence of phrenic nerve stimulation, the start of a respective occurrence of phrenic nerve stimulation being the time when the stimulation signal begins being sent;

in case the monitoring unit is configured for commanding phrenic nerve stimulation, the monitoring unit directly determines the start of each respective occurrence of phrenic nerve stimulation (as the monitoring unit itself sets said start);

in case the monitoring unit is configured for being used in conjunction with a control unit that commands phrenic nerve stimulation, the monitoring unit is configured for communicating with the control unit and receiving from the control unit information that enables identifying the start of each respective occurrence of phrenic nerve stimulation;

the monitoring of the electrical activity of the diaphragm of the human patient comprises processing the electrical signal captured by the one or more monitoring electrodes to detect an upcoming palsy of the right phrenic nerve (and/or of the right diaphragmatic dome); optionally, the unit is configured for outputting (e.g., real-time) an alert when detecting an upcoming palsy of the phrenic nerve;

the monitoring of the electrical activity of the diaphragm of the human patient comprises iteratively computing a value of a characteristic of the electrical signal captured by the one or more monitoring electrodes over a predetermined period of time following a respective occurrence of phrenic nerve stimulation;

the characteristic represents a diaphragmatic response intensity to phrenic nerve stimulation;

the characteristic is an amplitude of the electrical signal, for example a peak-to-peak amplitude (i.e., amplitude difference between two consecutives peaks of the electrical signal, that is, equaling the difference between a maximum intensity value of the electrical signal over the predetermined period of time and a minimal intensity value of the electrical signal over the predetermined period of time);

the characteristic is an area between an isoelectric line and a portion of a curve representing the electric signal over at least part of the predetermined period of time;

the predetermined period of time begins at or after the start of the respective occurrence of phrenic nerve stimulation, and/or ends at or before the start of the occurrence of the next (i.e., immediately subsequent) phrenic nerve stimulation;

the predetermined period of time begins at the start (e.g., +/−2 ms) of the respective occurrence of phrenic nerve stimulation or earlier than 12 ms or 10 ms after the start of the respective occurrence of phrenic nerve stimulation;

the predetermined period of time ends later than 40 ms or 45 ms after the start of the respective occurrence of phrenic nerve stimulation;

the predetermined period of time begins at the start (e.g., +/−2 ms) of the respective occurrence of phrenic nerve stimulation, and/or ends at 50 ms (e.g., +/−2 ms) after the start of the respective occurrence of phrenic nerve stimulation;

the unit is configured for detecting and/or outputting (e.g., real-time) an alert when the value of the characteristic (e.g., amplitude) decreases from a threshold value relative to a baseline, e.g., the threshold value being such that a decrease from the threshold value indicates a current or upcoming—e.g., right-diaphragmatic palsy, the threshold value being for example larger than 20% or 25% and/or smaller than 40% or 35%, for example 30% (e.g., +/−2%);

the monitoring of the electrical activity of the diaphragm of the human patient comprises computing a respective value of the characteristic for each occurrence of phrenic nerve stimulation; and/or the outputting of an alert is performed each time the value of the characteristic decreases from the threshold value relative to the baseline among a series of computed values of the characteristic, the series of computed characteristic values comprising each computed value of the characteristic (in other words the monitoring unit always outputs an alert when the threshold is reached for a computed value), or alternatively, the series of computed characteristic values comprising each computed value of the characteristic but excluding outlier values (in other words the monitoring unit always outputs an alert when the threshold is reached for a computed value, except for computed values that are deemed to be outliers);

each outlier value is a value of the characteristic that presents a deviation relative to the previous (i.e., immediately preceding) value of the characteristic larger than a predefined deviation threshold, wherein optionally the deviation threshold is larger than 15% and/or smaller than 25%, for example 20% (e.g., +/−2%);

the monitoring unit comprises or (respectively) is configured to be coupled to a display and/or a sound emitting device, and the monitoring unit is configured to perform or (respectively) trigger the outputting of the alert through the display and/or the sound emitting device; and/or additionally or alternatively, the monitoring unit is configured for monitoring diaphragmatic response to phrenic nerve stimulation according to a computer-implemented method which presents all or a combination of the features of any one of the computer-implemented methods for monitoring diaphragmatic response to phrenic nerve stimulation described in U.S. patent application Ser. No. 18/290,748, corresponding to publication WO 2023/001859 A1.

It is further provided a computer program comprising executable code which, when executed by a processor of the monitoring unit, causes the monitoring unit to receive and process an electrical signal captured by one or more intravascular monitoring electrodes, such as positioned in the inferior vena cava, so as to monitor the electrical activity of the diaphragm of the human patient. The executable code may optionally cause the unit to perform any one or any combination of the operations that the monitoring unit may be configured to perform.

It is further provided a (e.g., non-transitory) data storage medium having recorded thereon the computer program.

It is further provided a computer-implemented method for monitoring an electrical activity of the diaphragm of the human patient, the computer-implemented method being performed by the monitoring unit by executing the computer program. The computer-implemented method thus comprises receiving and processing an electrical signal captured by one or more intravascular monitoring electrodes, such as positioned in the inferior vena cava, so as to monitor the electrical activity of the diaphragm of the human patient. The computer-implemented method may optionally comprise performing any one or any combination of the operations that the unit may be configured to perform.

It is further provided a method of use of the apparatus. The method comprises introducing (via a minimally invasive medical procedure) the elongated part inside the inferior vena cava of a human patient, and positioning the elongated part at the operating location, such that the one or more monitoring electrodes are located in the inferior vena cava. The method comprises, while the elongated part is at the operating location, by the one or more monitoring electrodes, capturing an electrical signal. The electrical signal may represent an electrical activity of the diaphragm of the human patient, and the method may comprise monitoring said electrical activity, for example with the monitoring unit.

In examples, the method may further comprise performing a stimulation of the right phrenic nerve of the patient (via a minimally invasive medical procedure), while performing the monitoring of the electrical activity of the diaphragm of the human patient. In such a case, the monitoring of the electrical activity may comprise monitoring a diaphragmatic response to the phrenic nerve stimulation. The method may comprise detecting a time when the diaphragmatic response to the phrenic nerve stimulation indicates a current or upcoming (e.g., right) diaphragmatic palsy. The method may, upon such detection, comprise outputting an alert, for example a visual alert with a display and/or a sound alert with a sound emitting device.

In examples, the method may further comprise performing tissue ablation, such as ablation of atrial fibrillation (via a minimally invasive medical procedure), and while performing the ablation, performing the stimulation of the right phrenic nerve of the patient and the monitoring of the electrical activity of the diaphragm of the human patient. The ablation may comprise or consist of a cryoablation procedure, a radiofrequency ablation procedure, or an electroporation (or pulsed field ablation) procedure.

The method may comprise, upon detecting a time when the diaphragmatic response to the phrenic nerve stimulation indicates a current or upcoming (e.g., right) diaphragmatic palsy and/or upon outputting an alert (upon such detection), interrupting the ablation, either by (completely) stopping the ablation or pausing the ablation, in which latter case the method may comprise resuming the ablation after a lapse of time.

When the apparatus is structured according to the first embodiment, the elongated part of the apparatus includes the catheter, the distal portion of the elongated part includes an extremal portion of the catheter, and the extremal portion comprises an energy measurement and/or delivery tool, the method may optionally comprise performing the stimulation of the right phrenic nerve of the patient or the ablation of atrial fibrillation with the energy measurement and/or delivery tool of the apparatus, for example the one or more stimulation electrodes arranged on the extremal portion of the apparatus, or, the one or more radiofrequency or electroporation electrodes or the cryoballoon arranged on the extremal portion of the apparatus. The same apparatus is thereby used for performing the monitoring of the electrical activity of the diaphragm of the human patient, and meanwhile, for performing either the phrenic nerve stimulation or the tissue ablation. A separate apparatus may be used for performing the other one of phrenic nerve stimulation and the tissue ablation.

The method may use the monitoring unit, and optionally the (e.g., separate) control unit to perform any of these actions.

It is further provided a kit comprising the apparatus, the monitoring unit, and/or the data storage medium, and optionally a set of use instructions and/or a pointer to such use instructions (e.g., a URL, such as in the form of text, a hyperlink and/or a QR code), and further optionally the (e.g., separate) control unit. The use instructions and/or pointer may comprise text and/or pictograms, and/or arranged on a physical support, such as on paper (e.g., in a leaflet) and/or in a digital format (e.g., transportable data storage medium, such as a Universal Serial Bus flash drive, or downloadable from a server, such as a distant server or cloud service). The use instructions may comprise a description of the method and/or guidelines or directions for a user (medical practitioner) to perform the method. The kit may optionally further comprise an ablation device configured for atrial fibrillation ablation, for example an ablation catheter, such as a cryoablation (e.g., cryoballoon) catheter, a pulsed field ablation or electroporation catheter, or a radiofrequency ablation catheter, and/or a phrenic nerve stimulation device, for example a phrenic nerve stimulation catheter.

BRIEF DESCRIPTION OF THE DRAWINGS

Examples will now be described, by way of non-limiting illustration, and in reference to the accompanying drawings, where.

DETAILED DESCRIPTION

Figure 1:
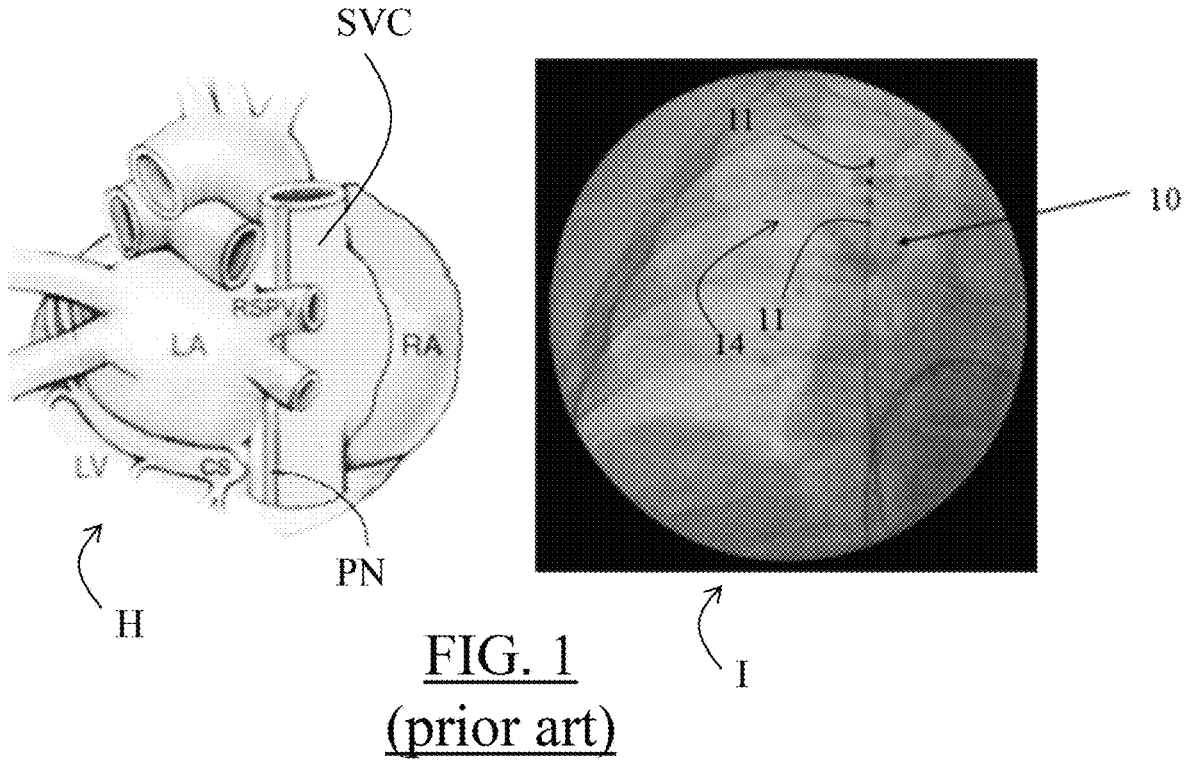
FIG. 1 illustrates the conventional manner in the prior art to perform phrenic nerve stimulation.

In the present disclosure, the following abbreviations are used for physical units: "ms" for milliseconds, "s" for seconds, "mm" for millimeters, "cm" for centimeters, and "V" for Volts, "mV" for millivolts. In the present disclosure, all distances are Euclidian distances, such that when referring to a distance between two positions, it is referred to the length of a straight segment joining the two positions.

The following discussion mainly focuses on the first embodiment, but all discussions not related to the distal portion of the elongated part being located in and/or beyond the right atrium of the patient according to the first embodiment also apply to the second embodiment.

The apparatus is provided for minimally invasive medical use. The apparatus may thus be (partly) introduced inside a human patient's body in a minimally invasive manner, so as to perform a medical-related procedure on the patient. In particular, the apparatus comprises an elongated part. The elongated part includes a catheter and/or a catheter sheath. The elongated part has a distal portion (e.g., containing an extremal portion of the elongated part, i.e., containing a distal end—i.e. extremum or tip—of the elongated part). The elongated part is configured for being introduced (in a minimally invasive manner) inside the inferior vena cava of a human patient, for example through the femoral vein and via an incision or puncture on the femoral vein, such as at the top of the patient's thigh (by the groin). The elongated part is configured for being positioned at a certain operating location, after introduction and longitudinal sliding movement inside the patient's vascular system, and in particular inside the inferior vena cava, and then, at least for the distal portion, inside the right atrium of the patient.

The elongated part may include one or more radiopaque markers, so as to correctly position the elongated part at the operating location, for example via fluoroscopy imaging. Additionally or alternatively, such positioning may be achieved via electrical mapping.

In the first embodiment, the operating location is by definition such that, when the elongated part is located at said operating location, the distal portion of the elongated part is located (e.g., entirely) in and/or (distally) beyond the right atrium of the patient (i.e., in the superior vena cava, in the right brachiocephalic vein, and/or in the right subclavian vein). The distal portion may be located entirely in the right atrium, entirely beyond the right atrium, or partly in the right atrium and partly beyond the right atrium. The distal portion of the elongated part may thereby be operated to perform any action medically relevant at such location. The distal portion may carry or embed any type of medical tool for that purpose. The operating location is further defined such that, when the elongated part is located at said operating location, an intermediate portion of the elongated part is (e.g., entirely) in the inferior vena cava. The intermediate portion is distinct (i.e., physically separate) from the distal portion, and the intermediate portion is located proximally relative to the distal portion. In the second embodiment, the operating location is by definition such that, when the elongated part is located at said operating location, the one or more monitoring electrodes are also positioned in the inferior vena cava.

The elongated part is thus flexible enough, long enough, and with a small enough diameter. For example, the elongated part's outer diameter (e.g., the catheter's or catheter sheath's diameter) may be equal or above to 4 Fr, and/or below or equal to 10 Fr, for example 6 Fr, 7 Fr or 8 Fr. The catheter's length may be above 90 cm and/or below 200 cm, for example equal to about 145 cm.

The apparatus further comprises one or more (intravascular) monitoring electrodes. The one or more monitoring electrodes are arranged on the intermediate portion of the elongated part in the first embodiment, and on the distal portion of the elongated part in the second embodiment. The one or more monitoring electrodes are configured for monitoring an electrical activity of the diaphragm of the human patient when the elongated part is positioned at the operating location. In other words, the one or more monitoring electrodes are configured to form at least one dipole which is configured for capturing a diaphragmatic compound motor action potential (CMAP) signal of the human patient, that is, an electric signal created by the contractions of the diaphragm of the human patient, and in particular of the right diaphragm of the human patient. The one or more monitoring electrodes may comprise a plurality of electrodes forming one or more pairs of electrodes (wherein distinct pairs may or may not share a same electrode), each pair being configured for being operated as such a dipole. Additionally or alternatively, the one or more monitoring electrodes may comprise one or more monitoring electrodes each configured for being operated as such a dipole with at least one other electrode which is not arranged on the intermediate portion of the elongated part. The at least one other electrode may comprise one or more monitoring electrodes each arranged on another portion of the elongated part, such as on the distal portion (in the first embodiment) or on a proximal portion of the elongated part (in both embodiments), and/or one or more monitoring electrodes each not arranged on and thus separate from the apparatus (e.g., comprising at least one intravascular electrode arranged on another apparatus and/or at least one extracorporeal electrode such as a skin and/or return electrode). Such captured electric signals may then serve in the methods of use of the apparatus in order to monitor the electrical activity of the diaphragm, for example with the monitoring unit.

When the elongated part of the apparatus is positioned at the operating location, the one or more monitoring electrodes are positioned in the inferior vena cava, thus near the diaphragm and in particular near the right diaphragmatic dome, due to the human anatomy. Therefore, the one or more monitoring electrodes are enabled to capture clearly (i.e., at a high intensity level) any electric signal generated by contraction of the diaphragm, and in particular the right diaphragmatic CMAP signal. Other electric signals commonly generated and that could possibly create interferences are captured by the one or more monitoring electrodes at a much lower intensity level, if even captured at all.

U.S. patent application Ser. No. 18/290,748 (corresponding to WO 2023/001859 A1) notably mentions the example of interferences created by the electrocardiogram (ECG) signal of the patient, and in particular by the QRS complex of the ECG signal. Such interferences (e.g., QRS far-field) can perturbate the monitoring of the electrical activity of the diaphragm of the human patient. The QRS far-field may in particular be captured at a large level by skin monitoring electrodes. But with the provided apparatus, thanks to the positioning of the one or more monitoring electrodes intravascularly inside the inferior vena cava when the elongated part is positioned at the operating location of the apparatus, thus relatively far from the heart, such interferences are negligible compared to the right diaphragmatic CMAP patterns (if at all present in the signal captured by the one or more monitoring electrodes). In particular, possible interferences due to the ECG and notably to the QRS complex are negligible. Thus, in examples, the series of computed values of the characteristic (e.g., amplitude) based on which the outputting of an alert is performed may include values computed on portions of the CMAP signal where the QRS interferes (that is, the QRS complex at least partially overlaps a CMAP pattern). Yet, even in such examples, the alert may accurately represent a true current or upcoming diaphragmatic palsy, that is, with little risk of false positives or false negatives, despite the perturbance created by the QRS concomitance.

Another potentially interfering signal may be an artefact in the CMAP signal, caused by the phrenic nerve stimulation. Such "stimulation artefact" (or "pacing artefact") may occur when the apparatus is used while performing phrenic nerve stimulation. At each stimulation signal sent to the (e.g., right) phrenic nerve, for example by a separate phrenic nerve stimulation catheter or by the apparatus itself (which may comprise a phrenic nerve stimulation tool on an extremal portion of its distal portion), the one or more monitoring electrodes may capture a respective peak, corresponding to a stimulation artefact. Thanks to the positioning of the one or more monitoring electrodes intravascularly inside the inferior vena cava when the elongated part is positioned at the operating location of the apparatus, thus relatively far from the heart, such stimulation artefact is relatively small compared to the CMAP pattern itself. Also, the stimulation artefact does not coincide or overlap with the CMAP pattern, as the CMAP occurs in response to the stimulation. The monitoring unit may thus relatively easily discriminate the stimulation artefact from the CMAP pattern. Thus, the computation of the characteristic can easily discard the stimulation artefact and thereby provide a value that accurately represents a true current or upcoming diaphragmatic palsy. This is in particular true when the computed characteristic is an amplitude of the electrical signal, such as a peak-to-peak amplitude. In that case, the minimal and maximal values of the portion of the signal captured by the one or more monitoring electrodes over a period of time following stimulation correspond to the CMAP, even if said portion of signal contains the stimulation artefact, due to it having a much lower amplitude than the CMAP pattern. Thus, the difference between those two values perfectly represents the diaphragmatic response.

In addition, due to the intravascular nature of the one or more monitoring electrodes, the provided apparatus captures the right diaphragmatic CMAP signal in a manner which is more robust to undesired movements during the medical procedure, compared to extracorporeal monitoring electrodes. Indeed, with extracorporeal monitoring electrodes, the captured CMAP signal could easily be affected by (even small) movements of the electrodes relative to the patient (e.g., caused by movements of the patient), and thereby present movement artefacts. This is because the fixation on the patient of extracorporeal electrodes, in particular skin electrodes, is less stable than the fixation of the intravascular monitoring electrodes of the provided apparatus. Besides, the operation of the apparatus in the first embodiment with the distal portion positioned in and/or beyond the right atrium further stabilizes the position of the one or more monitoring electrodes. In contrast, extracorporeal electrodes and in particular skin electrodes are exterior to the patient, each having a dedicated and lose cable, and the medical procedure may involve a team of medical practitioners in movement around the patient. This can lead to undesired movements of the extracorporeal electrodes.

Other issues with skin electrodes include artefacts that may be caused by undesired contacts with the electrodes prior to their use. For example, medical practitioners may contact the skin electrodes, such as during manipulation with their hands, and this may affect the sterile field and cause signal artefacts. Skin electrodes further provide a smooth CMAP signal, which makes it more difficult to interpret by the medical practitioner and/or in real-time.

Furthermore, the quality of the right diaphragmatic CMAP signal captured by extracorporeal monitoring electrodes depends on a correct placement of the electrodes on the patient's skin. Such correct placement is difficult to achieve, or otherwise can be imprecise, thus affecting said quality. In contrast, with the provided apparatus, the placement of the one or more monitoring electrodes is facilitated, as it is helpfully constrained radially by the diameter of the patient's vessels, and, in the first embodiment, longitudinally by the positioning of the distal portion in and/or beyond the right atrium.

In particular, the distal portion of the apparatus may comprise an expandable portion having an expanded configuration (e.g., the expanded configuration being a helical or spiral configuration, a loop configuration, a lasso configuration, or a basket configuration), and which may serve as an anchor by circumferentially fitting the inner wall of one or more local vessels, thereby providing ergonomics of placement to the practitioner, and stability of the placement. In the first embodiment, the one or more local vessels may comprise the right atrium and/or one or more vessels beyond the right atrium, for example the superior vena cava, the right brachiocephalic vein, and/or the right subclavian vein. In the second embodiment, the one or more local vessels may comprise the inferior vena cava.

By "expandable portion", it is meant that the portion is deformable such that its diameter (i.e., maximal width of the portion in a direction orthogonal to the catheter's longitudinal axis, that is, the cava vein's longitudinal axis) may be increased relative to the elongated part's diameter (i.e., the diameter of the non-expandable parts of the elongated part), possibly until fitting the vein's internal walls. The maximal diameter of the expandable portion (i.e., when fully expanded) may be above at least five times or even ten times the diameter of the catheter. The expandable portion may comprise the distal end of the distal portion of the elongated part, which is thus displaceable relative to the catheter's longitudinal axis. Alternatively, the expandable portion may be formed and end at a proximal location distinct from the distal end of the elongated part, which may thus remain on the elongated part's longitudinal axis when the expandable portion is expanded. The elongated part may be reversibly deformable between the expanded configuration and the non-expanded configuration. Thus, the operator may deploy the expandable portion to expand the elongated part inside the vena cava region vessel, operate the apparatus, and afterwards straighten back the expandable portion into the non-expanded configuration so as to pull out the catheter. The elongated part may be adjustably expandable. The operator may thus adjust the expandable portion to maintain the distal portion in a firm position of the vena cava, in particular a position wherein the distal portion is relatively close to the phrenic nerve. Alternatively, the expandable portion may be automatically expandable. In such a case, the expansion may only be triggered, and the catheter may self-deploy into the expanded configuration. The expandable portion may be configured to fit the inner wall of the vena cava or the inner wall of the right subclavian vein, for example circumferentially.

By "fit" the inner wall of a vein (i.e., any of the inner tissues branching from the vena cava to the right subclavian vein or brachiocephalic veins), it is meant that the expandable portion is configured to expand and achieve at least the diameter of the vein, so as to contact the inner wall of the vein and remain stable in position. For example, the expandable portion may present a diameter above 10 mm, 20 mm, 25 mm, 30 mm, 35 mm or 40 mm, for example of the order of 50 mm. This allows fitting the vena cava region vessel. The larger values of the expandable portion's diameter allow a more secure fit, in particular in the vena cava. The expansion may be adjustable. Thus, the operator may be enabled to deploy the expandable portion in the vena cava region vessel and adjust the expandable portion to the size thereof. Alternatively, the expansion may be non-adjustable, and for example triggering the expansion may allow the diameter to increase until constrained by the inner wall of the vena cava region vessel. The expandable portion may be made in a relatively soft material (for example as the rest of the elongated part), and thereby fit the vena cava region vessel with no harm thereto. Thanks to the expandable portion, the elongated part is easier to maintain in place and stable during operation, thereby improving ergonomics and stability of the phrenic nerve stimulation. The expandable portion may for instance have a diameter between 10 mm and 35 mm in the expanded configuration.

By "circumferentially fit", it is meant that the expandable portion fits a cross-sectional circular area of a volume. In other words, the expandable portion itself does not necessarily have a solid circle or a cylindrical or spherical volume, but it is appropriate to fit a cross-sectional circular area. Thus, the expandable portion is well suited for fitting the walls of a vein, which presents cross-sectional circular areas in the inner walls. This improves positional stability of the catheter. Indeed, the operator may expand the expandable portion within the walls of the vein (e.g., by manual adjustment or triggering of automatic deployment). The method may then comprise performing phrenic nerve stimulation and/or ablation (e.g., cryoablation or electroporation) while the catheter self-remains in a stable position. The circumferential fit may be such that the elongated part remains in position. In other words, the maximal diameter of the expandable portion may be higher than the diameter of the superior vena cava, of the right brachiocephalic vein, and/or of the right subclavian vein in the first embodiment, of the inferior vena cava in the second embodiment, such that a certain level of friction is achieved when the expandable portion is expanded, and the catheter thus substantially remains in place during its operation (unless a significant force is applied to overcome the friction). The expandable portion thus acts as an anchoring portion. The fitting indeed allows the vessel to retain the expandable portion, thus acting as an anchor.

Additionally or alternatively to being expandable, the elongated part may be deflectable at its distal portion. By deflectable, it is meant that the distal portion may be bent at least in one direction with respect to the body of the catheter. The maximal bending may be above 10 degrees and/or below 90 degrees. In examples, the maximal bending may be above 25 degrees, so as to allow positioning of the expandable portion to the right subclavian vein. The elongated part may comprise a pull-wire to impart deflection.

In an example, the elongated part may comprise a non-expandable distal end after the expandable portion. In other words, the non-expandable distal end does not expand and so remains in its original shape when the catheter expands. In a particular example, the non-expandable distal end may be straight, and stay straight in the axis of the catheter (i.e., the axis of the vena cava region vessel) even when the catheter is in the expanded configuration. The non-expandable distal end may for example have a length higher than 1 cm, and/or lower than 12 cm, for example between 1.5 cm and 4 cm.

In a specific implementation, the apparatus comprises a catheter and the distal portion of the catheter comprises a helical or spiral expandable portion configured to circumferentially fit the inner wall of the superior vena cava (VC), of the right brachiocephalic vein, and/or of the right subclavian vein, so as to remain in position during phrenic nerve stimulation. The catheter may or may not further comprise a non-expandable distal end (or tip) distally located after the expandable portion. The distal end (if any) may for example be straight, and/or have a length higher than 1 cm, and/or lower than 12 cm, for example between 1.5 cm and 4 cm. The expandable portion may have at most two coils in the expanded configuration. The expandable portion may have a diameter between 10 mm and 35 mm in the expanded configuration, i.e., an unconstrained expanded configuration. Additionally, the catheter may comprise a lumen for introducing a retractable inner straightening member. The catheter may further comprise the inner straightening member inside the lumen. The inner straightening member may be a guidewire. The guidewire may be metallic, may present a diameter above 0.030" and/or below 0.040", for example equal to 0.032" or to 0.035", and/or may be made of a hydrophobic material. The distal portion may comprise one or more phrenic nerve stimulation electrodes.

As a result of the increased stability and positioning facility offered by such the provided apparatus, the signal captured by the one or more monitoring electrodes represents relatively accurately the diaphragmatic CMAP signal and in particular of the right diaphragmatic CMAP signal. Thus, when used in a method which comprises performing a stimulation of the right phrenic nerve of the patient (via a minimally invasive medical procedure), while performing the monitoring of the electrical activity of the diaphragm of the human patient, the signal captured by the one or more monitoring electrodes represents a clean and non-noisy version of the right diaphragmatic CMAP signal. The apparatus thus enables an accurate monitoring of the electrical activity of the diaphragm of the human patient, and in particular of the right diaphragmatic dome's contraction response to right phrenic nerve stimulation.

When the method further comprises detecting (e.g., automatically, e.g., by the monitoring unit) a time when the diaphragmatic response to the phrenic nerve stimulation indicates a current or upcoming (e.g., right) diaphragmatic palsy, the apparatus enables securing any ongoing medical procedure (e.g., ablation of atrial fibrillation, such as a cryoablation procedure, a radiofrequency ablation procedure, or an electroporation or pulsed field ablation procedure) and preventing or reducing risks or consequences of right phrenic nerve injury possibly caused by said ongoing medical procedure. The method may indeed comprise, upon detecting a time when the diaphragmatic response to the phrenic nerve stimulation indicates a current or upcoming (e.g., right) diaphragmatic palsy, interrupting the ablation, for example by permanently stopping the medical procedure or by temporarily pausing the medical procedure (and resuming the medical procedure after a predetermined- and appropriate-lapse of time). The method may for example, upon detection of a current or upcoming (e.g., right) diaphragmatic palsy, comprise outputting an alert, for example a visual alert with a display and/or a sound alert with a sound emitting device. The monitoring unit may comprise or (respectively) be coupled to such display and/or sound emitting device, and thereby be configured to perform or (respectively) trigger said outputting of the alert. The alert allows medical practitioners to directly react and possibly interrupt the medical procedure. Thanks to the accuracy of the right diaphragmatic CMAP signal enabled by the provided apparatus, the method allows to prevent or reduce frequency of false positive events (i.e., an alert is outputted although there is no current or upcoming palsy) and/or of false negative events (i.e., no alert is outputted although there is a current or upcoming palsy).

Besides, in the first embodiment, the one or more monitoring electrodes are arranged on the intermediate portion of the same elongated part which includes a catheter and/or a catheter sheath and that also has a distal portion which can be used for any type of medical action(s). The distal portion may carry or embed any type of medical tool for that purpose. The proposed solution thus avoids the need for a separate apparatus dedicated to the monitoring of the electrical activity of the diaphragm, thereby reducing the quantity of material and equipment involved in the medical procedure, while also avoiding the need for a separate incision or puncture on the femoral vein and reducing obstruction caused by the multiplication of apparatuses inside the patient's vascular system. The medical procedure is thus eventually particularly minimally invasive.

In an example, the elongated part may include a catheter having an extremal portion (i.e., a distal portion containing the extremum or tip of the catheter) which comprises (e.g., carries or embeds) an energy measurement and/or delivery tool. By "energy measurement and/or delivery tool", it is meant herein any tool or device that allows at least one of the measurement of an energy (e.g., including capturing an electric signal, capturing an ultrasound signal, and/or quantifying a local temperature or other energy-related property), and the delivery of an energy (e.g., including emitting an electric signal, applying a heat, and/or applying a cold temperature). In such example, when the elongated part is positioned at the operating location, the apparatus may be operated to perform with the distal portion an energy measurement and/or delivery in and/or beyond the right atrium, and meanwhile, to capture with the one or more monitoring electrodes an electric signal which accurately represents the (e.g., right) diaphragmatic CMAP signal, so as to enable monitoring of the electrical activity of the diaphragm of the patient. The delivery and the capturing may be simultaneous or interlaced.

The energy measurement and/or delivery tool may comprise one or more (energy measurement and/or delivery) electrodes, one or more probes, and/or one or more cryotherapy delivery tools.

The energy measurement and/or delivery tool may be configured for performing a stimulation, for example a right phrenic nerve stimulation, for performing a tissue ablation, such as an atrial fibrillation ablation, for example by radiofrequency energy, by pulsed field ablation (or electroporation), or by cryoablation, for performing an ultrasound treatment, or for performing a cardiography, for example an echocardiography, an intracardiac echocardiography, or an ultrasound cardiography.

The energy measurement and/or delivery tool may comprise said one or more (energy measurement and/or delivery) electrodes, and these may be configured for said performing of a stimulation, for example a right phrenic nerve stimulation, for performing a tissue ablation, such as an atrial fibrillation ablation, for example by radiofrequency energy or by pulsed field ablation (or electroporation), for performing an ultrasound treatment, or for performing a cardiography, for example an echocardiography, an intracardiac echocardiography, or an ultrasound cardiography.

The energy measurement and/or delivery tool may comprise said one or more probes, and these may be configured for said performing of a cardiography, for example an echocardiography, an intracardiac echocardiography, or an ultrasound cardiography.

The energy measurement and/or delivery tool may comprise said one or more cryotherapy delivery tools, and these may be configured for said performing of a cryoablation. The one or more cryotherapy delivery tools may notably comprise a cryoballoon.

The elongated part may include a catheter having an extremal portion which comprises the energy measurement and/or delivery tool. The extremal portion may comprise an expandable portion as described earlier, and the energy measurement and/or delivery tool may be arranged on the expandable portion configuration. For example, the energy measurement and/or delivery tool may comprise one or more electrodes arranged on the expandable portion configuration (e.g., on the helix, spiral, loop, basket, or lasso formed on the catheter when in the expanded configuration). This enables contact between the energy delivery tool and body tissue, thereby improving its function, while offering an anchoring to the catheter, thereby facilitating positioning and improving stability of the one or more monitoring electrodes at the same time.

In a first realization of the example where the elongated part includes a catheter having an extremal portion which comprises an energy measurement and/or delivery tool, the energy measurement and/or delivery tool may comprise one or more stimulation electrodes configured for stimulation of the right phrenic nerve, and the catheter is configured to be introduced in the superior vena cava of the human patient so as to position the one or more stimulation electrodes in the superior vena cava, in the right brachiocephalic vein, and/or in the right subclavian vein. In this realization, the same apparatus may be used for both stimulating the phrenic nerve with the stimulation electrodes arranged on the distal portion of catheter, and for monitoring the right diaphragmatic response to said stimulation with the one or more monitoring electrodes arranged on the intermediate portion of the elongated part (e.g., of the same stimulation catheter or of a catheter sheath covering said stimulation catheter). The use of the same apparatus to perform the stimulation and the related response monitoring facilitates said monitoring and increases its accuracy. For example, the apparatus may be configured to be coupled to a monitoring unit which may control both the stimulation and the diaphragmatic response monitoring. This facilitates performing the monitoring of the electrical activity of the diaphragm of the human patient being as a function of a timing of the phrenic nerve stimulation, since the same monitoring unit sets said timing (and thereby necessarily directly knows when each phrenic nerve stimulation starts). In such a first realization, the apparatus may be used in conjunction with another and separate apparatus that performs a therapy, for example an ablation catheter, such as for atrial fibrillation ablation, for instance a radiofrequency ablation catheter, a pulsed field ablation catheter, or a cryotherapy or cryoballoon catheter.

In examples of the first realization, the extremal portion may comprise an expandable portion as described earlier, and the one or more stimulation electrodes may be arranged on the expandable portion configuration. This may enable contact between the one or more stimulation electrodes and body tissue (e.g., the one or more stimulation electrodes for example comprising one or more ring electrodes), and thereby improving right phrenic nerve stimulation, while offering an anchoring to the catheter, thereby facilitating positioning and improving stability of the one or more monitoring electrodes as well.

In another and second realization of the example where the elongated part includes a catheter having an extremal portion which comprises an energy measurement and/or delivery tool, the energy measurement and/or delivery tool may comprise one or more tools configured for performing a therapy, for example one or more ablation tools (e.g., ablation electrode(s) or cryoballoon) configured for performing tissue ablation such as atrial fibrillation ablation. The catheter may for example be a radiofrequency ablation catheter, a pulsed field ablation catheter, or a cryotherapy or cryoballoon catheter. In this realization, the same apparatus may be used for both performing the therapy (e.g., ablating tissue), and for monitoring the right diaphragmatic activity, for example in response to a phrenic nerve stimulation, with the one or more monitoring electrodes arranged on the intermediate portion of the elongated part (e.g., of the same ablation catheter or of a catheter sheath covering said ablation catheter). In such a second realization, the apparatus may be used in conjunction with another and separate apparatus that performs a right phrenic nerve stimulation.

In examples of the second realization, the extremal portion may comprise an expandable portion as described earlier, either formed by the cryoballoon or by a shape modification of the catheter (e.g., the expanded configuration being a helical or spiral configuration, a loop configuration, a lasso configuration, or a basket configuration). In the latter case, the catheter may include one or more (e.g., radiofrequency or electroporation) ablation electrodes arranged on the expandable portion configuration. This may enable contact between the energy delivery tool and body tissue (e.g., the one or more ablation electrodes for example comprising one or more ring electrodes), and thereby improving ablation, while offering an anchoring to the catheter, thereby facilitating positioning and improving stability of the one or more monitoring electrodes as well.

In yet another and third realization of the example where the elongated part includes a catheter having an extremal portion which comprises an energy measurement and/or delivery tool, the energy measurement and/or delivery tool may be configured for performing a cardiography, for example an echocardiography, an intracardiac echocardiography, or an ultrasound cardiography, and the energy measurement and/or delivery tool may comprise one or more probes therefore. The catheter may for example be a probing catheter. In this realization, the same apparatus may be used for both performing the probing, and for monitoring the right diaphragmatic activity, for example in response to a phrenic nerve stimulation, with the one or more monitoring electrodes arranged on the intermediate portion of the elongated part (e.g., of the same probing catheter or of a catheter sheath covering said probing catheter). In such a third realization, the apparatus may be used in conjunction with another and separate apparatus that performs a right phrenic nerve stimulation, and/or with another and separate apparatus that performs a tissue ablation (e.g., a radiofrequency ablation catheter, a pulsed field ablation catheter, or a cryotherapy or cryoballoon catheter).

In examples of the third realization, the extremal portion may comprise an expandable portion as described earlier, and the energy measurement and/or delivery tool may be arranged on the expandable portion so as to enable contact with body tissue, and thereby improving probing, while offering an anchoring to the catheter, thereby facilitating positioning and improving stability of the one or more monitoring electrodes as well.

The following discusses the one or more monitoring electrodes arranged on the elongated part of the apparatus.

Each monitoring electrode is an intravascular electrode, meaning that it consists of a unitary conductive portion of the elongated part which is open to the outside vessel tissue and/or vessel liquids, and connectable to a pole. At least one (e.g., each) monitoring electrode of the apparatus may be made of a conductive material, for example metallic, such as gold, platinum, silver, and/or any adequate alloy. The apparatus may comprise one or more electrical leads, the one or more electrical leads being configured for receiving electricity from each monitoring electrode. At least one (e.g., each) electrical lead may be an electrical wire, for example arranged inside the apparatus in one or more lumens, or a conductive path of electrical substrate formed on a surface of the apparatus, for example an inner surface of the apparatus. The apparatus may comprise an electrical connector for (e.g., removably) connecting the apparatus to the monitoring unit or to an electrical cord or cable connectable to said monitoring unit, so as to receive electrical signals from each monitoring electrode via the one or more electrical leads.

At least one (e.g., each) monitoring electrode may present a ring shape formed peripherally on the external surface of the apparatus. In an example, the one or more monitoring electrodes comprise or consist of one or more ring electrodes. This makes the well-functioning of the apparatus independent of which radial angle is used for the positioning of the elongated part inside the inferior vena cava. Additionally or alternatively, instead of a ring, at least one (e.g., each) monitoring electrode of the apparatus may present the shape of a pad (i.e., isolated block of conductive material delimited by one single curve) formed on an external surface of the apparatus and facing at least part of the walls of the vein. The pad may present any geometry, for example a square shape, a circle shape, or any elongated shape with a length higher than a width, such as a generally rectangular shape, or yet a generally elliptic shape. By "length" respectively "width" of the pad, it is meant the maximal respectively minimal distance between a pair of points of the pad when projected on a plane generally parallel to the pad.

At least one (e.g., each) monitoring electrode may present a length (i.e., in the longitudinal direction of the elongated part) higher than 0.1 mm and/or lower than 20 mm, for example higher than 0.5 mm and/or lower than 5 mm, for example equal to 2 mm (e.g., +/−0.5 mm). This provides sufficient conductive surface for an accurate and robust monitoring, while not affecting flexibility of the elongated part.

The one or more monitoring electrodes may comprise a plurality of individual electrodes electrically disconnected one from the other and thus operable independently one from the other. Optionally, each such individual monitoring electrode may be connected to the monitoring unit via its own dedicated electrical lead (e.g., electrical wire or conductive path), such that the apparatus may comprise a plurality of electrical leads (e.g., electrical wires and/or conductive paths) each dedicated to a respective monitoring electrode. The one or more monitoring electrodes thus comprise at least two individual electrodes configured to form a dipole, where each individual electrode has a respective electrical lead and the two leads are connectible to different poles of the monitoring unit.

The one or more monitoring electrodes may comprise at least three individual electrodes, configured for forming several pairs (e.g., at least two or three pairs) of individual electrodes each configured to form a dipole. The apparatus may be configured for selecting any given pair to form a dipole for the monitoring of the diaphragmatic electrical activity., for example an optimal pair (e.g., the pair for which the signal is the most intense). The remaining electrodes may be deactivated. Optionally, one of the remaining electrodes may be used as a bias electrode (or reference electrode). The one or more monitoring electrodes may thereby comprise at least one or at least two individual electrodes each configured for both either forming a monitoring dipole with another individual electrode, or being used as a bias or reference electrode (while another pair of individual electrodes is used for the moinitoring).

The one or more monitoring electrodes may comprise at least one monitoring electrode arranged on an external surface of the elongated part (when the elongated part is at the operating location and the apparatus is in use). Optionally, when the elongated part is at the operating location and the apparatus is in use, each monitoring electrode is arranged on an external surface of the elongated part. This enables contact with vessel tissue and/or vessel liquids, and thereby enhances the accuracy of the electrical signal captured by the at least one monitoring electrode.

If the elongated part comprises a catheter but no catheter sheath (e.g., the elongated part consists of a sheath-less catheter), the at least one monitoring electrode may be arranged on an external surface of the catheter shaft. In such a case, the at least one monitoring electrode is directly in contact with the outside. Such a sheath-less catheter may be used in conjunction with an introduction member, such as a guidewire or inner straightening member or a separate introducer sheath.

If the elongated part comprises a catheter sheath but no catheter, the at least one monitoring electrode may be arranged on an external surface of the catheter sheath. The catheter sheath may be provided to be used in conjunction with a catheter during the medical procedure, and the at least one monitoring electrode may be adequately positioned on the catheter sheath to fall at the right position for diaphragmatic nerve monitoring during the procedure.

If the elongated part comprises both a catheter sheath and a catheter shaft, the at least one monitoring electrode may be arranged on an external surface of the catheter sheath as above, or alternatively, on an external surface of the catheter shaft. In such a case, the catheter sheath may be withdrawable, meaning that it can be withdrawn at least from a length sufficient to leave uncovered the portion of the catheter shaft carrying the one or more monitoring electrodes.

The catheter may comprise positioning means. For example, the catheter may comprise a (e.g., metallic) guidewire configured for guiding the catheter to the vena cava. The guidewire may be arranged in an internal lumen of a body of the catheter and exit a distal extremity of the catheter body. The guidewire may present a diameter above 0.020" and/or below 0.060", preferably above 0.030" and/or below 0.040", for example equal to 0.032" or to 0.035". The guidewire may be inserted in a hemostatic valve. The catheter may further comprise a flushing lumen. In an example, the guidewire is made of a hydrophobic material. Alternatively, the catheter may have a body which comprises an internal lumen configured for insertion of a positioning mandrel. The lumen may be closed at the distal end of the catheter body, such that the mandrel cannot exit the catheter body. The apparatus may additionally comprise such mandrel.

Figure 2:
FIG. 2 shows a real CMAP signal of a human patient obtained while the patient undergoes right phrenic nerve stimulation with an experiment performed according to the prior art.
Figure 3:
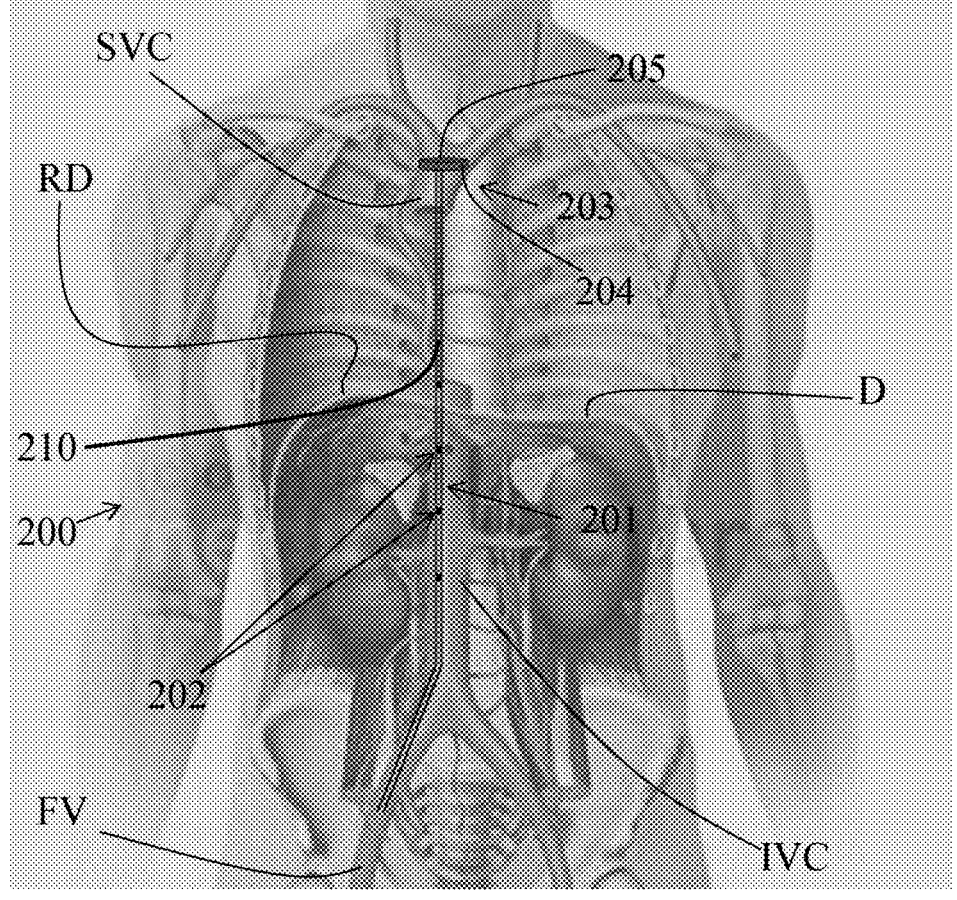
FIG. 3 shows an example of the apparatus of the disclosure introduced inside the thorax of a human patient.
Figure 4:
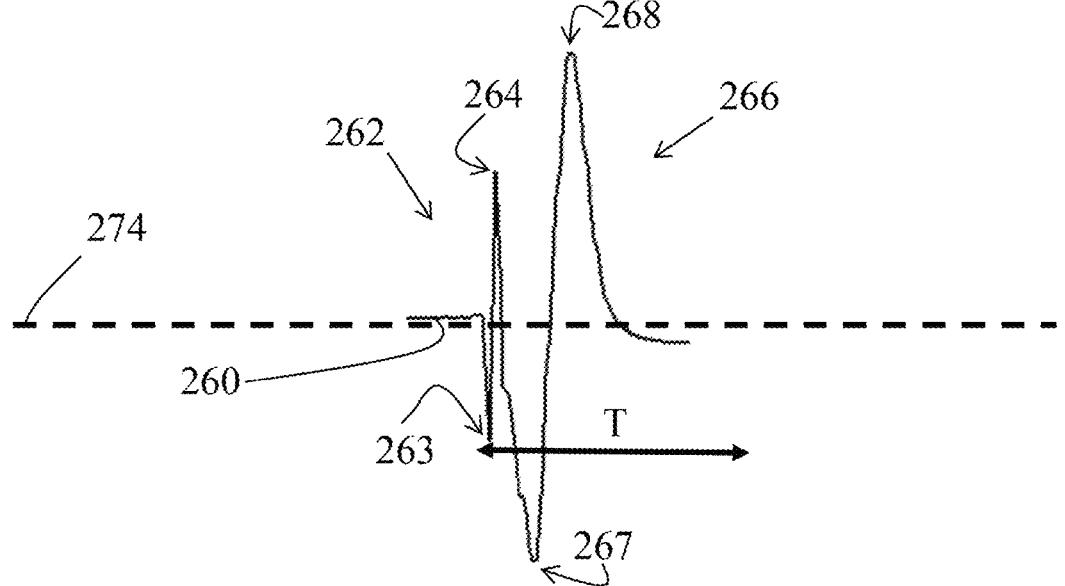
FIG. 4 shows a CMAP signal obtained using the apparatus of the disclosure and the monitoring unit of the disclosure.

Referring to FIGS. 2-4, the improvement of the monitoring of the electrical activity of the diaphragm of the human patient offered by the disclosure is illustrated and discussed.

FIG. 2 shows a real CMAP signal 250 of a human patient obtained while the patient undergoes right phrenic nerve stimulation at separate times, with an experiment performed according to the prior art, that is, using skin electrodes placed on the patient's thorax. The figure shows one period of the signal, that is, corresponding to a single stimulation signal. As can be seen, the CMAP signal 250 is quite noisy, and the CMAP pattern 256 is relatively small in amplitude, compared to the stimulation artefact 252. This makes it difficult to process the CMAP signal 250 so as to monitor the electrical activity of the patient's diaphragm. As a result, this technique can lead to inaccuracies or delays in detecting an upcoming palsy of the diaphragm, with the consequence that the phrenic nerve may be injured or more severely injured if the stimulation is accompanying an ablation procedure.

FIG. 3 shows an example of the apparatus introduced inside the thorax of a human patient. As can be seen, the inferior vena cava IVC is against and goes through the diaphragm D of the patient, and in particular through the right diaphragmatic dome RD. Thus, by introducing inside the inferior vena cava IVC, e.g., through the femoral vein FV, an apparatus 200 according to the disclosure which has one or more monitoring electrodes 202 arranged on an elongated part 210 of the apparatus 200, and by positioning the apparatus 200 at an operating location where the one or more monitoring electrodes 202 are in the inferior vena cava IVC, one can capture a cleaner CMAP signal, more robust to patient's movements or undesired manipulations, with facilitated positioning of the one or more monitoring electrodes 202, and where CMAP patterns are prominent relative to potential interferences such as QRS complexes (i.e., "QRS far field" interference) or stimulation artefacts (or "pacing" artefacts), and thus much less affected by such potential interferences. This allows improving the processing of the CMAP signal and providing a more accurate and timely prediction of upcoming diaphragmatic palsies.

As further shown on FIG. 3, the elongated part 210 of the apparatus 200 may comprise or consist of a catheter and/or have a distal portion 203 which, when the apparatus 200 is at the operating location such as shown on the figure, falls in and/or beyond the right atrium, such as inside the superior vena cava SVC in the example shown on the figure (but which is not limiting in this respect). The one or more monitoring electrodes 202 are thus arranged on an intermediate portion 201 of the elongated part/apparatus 200, proximal to the distal portion 203 relative to the femoral vein FV. This is however merely an example, and the apparatus 200 may alternatively comprise or consist of another type of catheter, or consist of a catheter sheath to be used in conjunction with a catheter.

As further shown on FIG. 3, the distal portion 203 may optionally comprise an expandable portion 204 having an expanded configuration (which is a lasso configuration on the figure, but which may alternatively be any other type of expanded configuration, such as a helical or spiral configuration, a loop configuration, or a basket configuration) so as to be circumferentially fitted to the inner wall of the vessel in which the distal portion 203 is positioned at the operating location. This vessel is the superior vena cava SVC in the example shown on the figure, but this principle more generally applies to the right atrium or any other vessel beyond the right atrium, such as the superior vena cava, the right brachiocephalic vein, and/or the right subclavian vein. The expandable portion may optionally be configured for a circumferential fit in several vessels, optionally simultaneously (whereby part of the expandable portion is in a first vessel, and another part of the expandable portion is second vessel which joins the first vessel). Such circumferential fit facilitates positioning of the apparatus 200 at the operating location. This also stabilizes the apparatus 200 and thus prevents or reduces undesired movements of the one or more monitoring electrodes 202 during the capturing and monitoring of the CMAP signal. Thus, this further improves the processing of the CMAP signal and further enhances accuracy and timely prediction of upcoming diaphragmatic palsies. Alternatively to having an expandable portion, the catheter may be a straight catheter. In such a case, the catheter may optionally be deflectable.

The distal portion 203 may additionally or alternatively comprise or form an energy measurement and/or delivery tool as described earlier (not shown on the figure). This allows, using the same apparatus 200 and thus the same puncture through the femoral vein FV, performing a medical operation involving energy measurement and/or delivery (e.g., such as right phrenic nerve stimulation, or, atrial fibrillation ablation) where the distal portion 203 is positioned at the operating location. The distal portion 203 (e.g., the extremal/expandable portion 204) may for example form or carry the energy measurement and/or delivery tool. The distal portion 203 (e.g., the extremal/expandable portion 204) may for example carry one or more stimulation electrodes. In the illustrated configuration, such one or more stimulation electrodes would perform effective right phrenic nerve stimulation. The catheter 210 of the figure may indeed be positioned such that the distal portion 203 (e.g., the extremal/expandable portion 204) is located in or beyond the superior vena cava SVC (as shown on the figure, in the SVC where the superior vena cava SVC divides into the right and left brachiocephalic veins). Alternatively, the distal portion 203 or expandable portion 204 may comprise one or more (radiofrequency or electroporation) ablation electrodes or a cryoballoon, and the catheter 210 may be configured to be positioned at the ostium of or inside a pulmonary vein.

As further shown on FIG. 3, the one or more monitoring electrodes 202 may comprise at least two electrodes that are arranged at different longitudinal positions of the intermediate portion 201 (i.e., each electrode 202 being arranged at a respective longitudinal position different from the other electrode(s) 202). This provides a whole length of the elongated part 210 useful for the monitoring.

Said at least two monitoring electrodes 202 may further be configured to form a dipole that captures the electrical activity of the diaphragm D and in particular of the right diaphragmatic dome RD, so as to monitor said activity with the monitoring unit. When such a dipole is formed between at least two monitoring electrodes 202, the at least two monitoring electrodes 202 are configured for capturing the electrical signals generated by diaphragmatic contractions, with the use of any other electrode to perform such monitoring, and in particular without the use of any extracorporeal electrode. Such a dipole of monitoring electrodes 202 is moreover arranged vertically, that is, orthogonal to the diaphragmatic dome and thus to the direction of its contractions (e.g., in response to phrenic nerve stimulation). As a result, such a dipole offers an optimal spatial configuration to capture the electrical signals generated by such contractions, thus providing a particularly clean and high-intensity CMAP signal.

As further shown on FIG. 3, the one or more monitoring electrodes 202 may comprise more than two electrodes that are arranged at different longitudinal positions of the intermediate portion 201 (i.e., each electrode 202 being arranged at a respective longitudinal position different from the other electrode(s) 202), for example three monitoring electrodes 202, four monitoring electrodes 202 (as illustrated on the figure), or more. This facilitates having at least two electrodes positioned optimally to capture a clean and high-intensity CMAP, for example at least two electrodes positioned beneath the right diaphragmatic dome RD but still inside the inferior vena cava IVC. This allows capturing the diaphragmatic electrical activity at a location relatively far from the heart, thus with little impact of QRS complexes on the captured signal.

Optionally, the apparatus 200 and/or the monitoring unit may be configured to select any pair of individual monitoring electrodes 202 to form the dipole that captures the diaphragmatic electrical activity, all other monitoring electrodes 202 being deactivated (i.e., "silenced") during said monitoring, with optionally one of said other monitoring electrodes 202 being used as a reference or bias electrode. This allows selecting an optimal dipole, to capture a cleanest and highest-intensity CMAP out of several possibilities.

Additionally or alternatively, the one or more monitoring electrodes 202 may be arranged so that, for a proportion of human patients above 90% or 95%, at least one electrode 202 lies beneath the right diaphragmatic dome RD, but still inside the inferior vena cava IVC (e.g., and relatively near the right diaphragmatic dome RD). The plurality of monitoring electrodes 202 may further be arranged so that, for a proportion of human patients above 90% or 95%, at least two electrodes 202 (e. g., configured to form a dipole) lie beneath the right diaphragmatic dome RD, but still inside the inferior vena cava IVC (e.g., and relatively near the right diaphragmatic dome RD). In other words, the one or more monitoring electrodes 202 may be arranged so as to correspond to a widest range of anatomies among the human population.

For example, the at least two monitoring electrodes 202 (e. g., configured to form a dipole) may comprise a first monitoring electrode 202 at a distance from a second monitoring electrode 202 higher than or equal to 1 cm and/or lower than or equal to 20 cm, for example between 5 cm and 10 cm. Such a spacing allows to form a dipole which captures a clean and high-intensity CMAP signal, while not being too large and thus allowing the presence of more than two monitoring electrodes 202 on a useful length of the elongated part 210, to optimize placement and/or selection of an appropriate dipole. The distance separating longitudinally each pair of consecutive electrodes 202 may optionally be constant (i.e., the electrodes 202 are regularly spaced).

In particular, the apparatus 200 may comprise more than two or more than three electrodes 202 located at different longitudinal positions, each pair of electrodes 202 being spaced by a distance between 5 cm and 10 cm, and the apparatus 200 may be configured to form dipoles (e.g., selectively) between one or more pairs of consecutive electrodes 202 and/or between one or more pairs of electrodes 202 having one or two electrodes 202 therebetween.

The arrangement of the one or more monitoring electrodes 202 on the elongated part 210 may in an example be further specified referring to a distal end 205 of the elongated part 210, wherein the distal end 205 is the distal extremity point of the elongated part. The one or more monitoring electrodes 202 may in particular comprise at least one electrode 202 arranged (or the apparatus 200 may be configured for reaching such arrangement), when the elongated part 210 is at the operating location (e.g., and in the expanded configuration), at a distance from the distal end 205 higher than or equal to 10 cm and/or lower than or equal to 50 cm, for example between 15 cm and 30 cm. The one or more monitoring electrodes 202 may further comprise several electrodes 202 arranged (or the apparatus 200 may be configured for reaching such arrangement), when the elongated part 210 is at the operating location (e.g., and in the expanded configuration), at a distance from the distal end 205 higher than or equal to 10 cm and/or lower than or equal to 50 cm, for example two, three or four electrodes 202 arranged at a distance from the distal end 205 higher than or equal to 10 cm and/or lower than or equal to 50 cm, for example two, three or four electrodes 202 arranged at a distance from the distal end 205 between 10 cm and 50 cm, for example four electrodes 202 arranged at a distance from the distal end 205 between 10 cm and 50 cm.

In a specific realization, the apparatus 200 may comprise a catheter having an expandable portion on its extremal portion, and when the apparatus is in the expanded configuration and straightened elsewhere, the first encountered monitoring electrode 202 (starting from the distal end 205 and going proximally along the elongated part 210) is at a distance from the distal end 205 of 20 cm (e.g., +/–2 cm), each next electrode 202 is at a distance from the preceding electrode 202 of 8 cm (e.g., +/–1.5 cm), and there are more than three (for example four) electrodes 202.

FIG. 4 shows a CMAP signal 260 obtained using the provided apparatus and the provided monitoring unit, such as apparatus 200 of FIG. 3. As can be seen, the CMAP signal 260 is clean, i.e., non-noisy, and the CMAP pattern 266 is prominent and well-separated from the stimulation artefact 264.

More precisely, the figure shows a baseline response to one occurrence of right phrenic nerve stimulation. The emission of the stimulation signal reaches almost real-time the right phrenic nerve and generates in the CMAP signal 260 a stimulation artefact 262 soon after. The stimulation artefact 262 has a first peak 263 and a second peak 264 of opposite second derivative signs (i.e., one peak being a local minimum and the other peak being a local maximum). On the figure, the first peak 263 is negative while the second peak 264 is positive, but this merely depends on the polarity of the dipole of monitoring electrodes 202 capturing the CMAP and could thus be equivalently inverted. Following soon after the stimulation artefact 262, the CMAP signal 260 includes a CMAP pattern 266 which has a first peak 267 (occurring about 15 ms+/–3 ms after the stimulation signal is sent) and a second peak 268 (occurring about 35 ms+/–5 ms after the stimulation signal is sent) of opposite second derivative signs (i.e., one peak being a local minimum and the other peak being a local maximum).

Thus, when computing the peak-to-peak amplitude of the signal 260 over the whole period shown on the figure, one computes the difference between the intensity of the signal at peak 268 and the intensity of the signal at peak 267, since these peaks are the two extrema of the signal 260 over the period. This very simply computation thus directly and very accurately represents the diaphragmatic response intensity to phrenic nerve stimulation. In another example, when computing the area between an isoelectric line 274 and the curve 260 over the period of time shown on the figure, one still obtains an accurate representation of the diaphragmatic response intensity to phrenic nerve stimulation, as the contribution of the stimulation artefact 262 to the area computation is relatively low and can thus be neglected. The provided apparatus thus allows to compute a representation of the diaphragmatic response intensity to phrenic nerve stimulation from the CMAP signal 260 in a facilitated manner, without any specific processing to remove the stimulation artefact 264, and without any specific processing or setting to manage the QRS far-field (as interference therefrom can be neglected).

As a result, the monitoring of the electrical activity of the diaphragm may comprise computing a baseline value of any such characteristic representative of diaphragmatic response intensity to phrenic nerve stimulation on the CMAP signal 260 captured by the one or more monitoring electrodes 202. As known per se, the baseline value represents the value of the characteristic when the patient is at rest, i.e., not subjected to the ablation procedure, and may be obtained by performing phrenic nerve stimulation before starting the ablation procedure, e.g., and averaging obtained values (in any manner). The monitoring may then comprise, e.g., after the ablation procedure or any other medical procedure has started, computing the value of the characteristic at respective occurrences of phrenic nerve stimulation, and detecting and/or outputting an alert when the value of the characteristic decreases from a threshold value relative to the baseline value, e.g., the threshold value being such that a decrease (or drop) from the threshold value indicates a current or upcoming—e.g., right-diaphragmatic palsy, the threshold value being for example larger than 20% or 25% and/or smaller than 40% or 35%, for example 30% (e.g., +/–2%). The monitoring thus detects and/or alerts on upcoming palsies in a simplified and more accurate manner.

Now, since the phrenic nerve stimulation is commanded by the medical team, for example through settings of the monitoring unit or any separate control unit, the monitoring unit is aware of the timing of the phrenic nerve stimulation. In particular, the monitoring unit can easily identify the starting time of each respective occurrence of phrenic nerve stimulation, which corresponds to an instant when the curve 260 distances itself from line 274 to reach the first peak 263 of the stimulation artefact 262. The monitoring may then comprise computing the value of the characteristic over a predetermined period T which begins at or soon after said starting time, and lasts for a duration that is known (from a medical standpoint) to encompass the diaphragmatic response.

In particular, the predetermined period of time T may begin at the starting time (e.g., +/−2 ms) of the occurrence of phrenic nerve stimulation or earlier than 12 ms or 10 ms after said starting time, so as to ensure that it begins before the CMAP pattern 266, and in particular before the first peak 267. The predetermined period of time T may end later than 40 ms or 45 ms after the starting time for example at about 50 ms after the starting time, so as to ensure that it ends after the CMAP pattern 266, and in particular after the second peak 268.

The predetermined period of time T may end before the starting time of the next occurrence of phrenic nerve stimulation. The phrenic nerve stimulation may be performed at a frequency of 60 times per minute, such that the predetermined period of time T may for example end before 900 ms or 500 ms or 100 ms after the starting time of the current occurrence, for example at about 50 ms after the starting time.

In one example, the monitoring method may comprise, at each occurrence of a phrenic nerve stimulation, computing the difference between the maximal value of the signal 260 and the minimal value of the signal 260, over a portion of the signal 260 that corresponds to the period of time T, without any further processing. The method thereby necessarily obtains, in most cases and without further processing of the signal during said calculation, the peak-to-peak amplitude value between peak 267 and 268, that is, a very accurate representation of the diaphragmatic response intensity. This provides a reliable value for performing the detection and/or alert output.

Optionally, in order to reduce false positives, before outputting an diaphragmatic palsy detection and/or an alert thereof, the monitoring unit may comprise testing whether the computed value is an outlier. The monitoring unit may then perform the output only when the computed value is not an outlier, and rather discard the value when the computed value is an outlier (i.e., the monitoring unit does nothing and waits for the next phrenic nerve stimulation occurrence).

An outlier value may be detected when the deviation relative to the preceding iteration of the computing is too high. In general, the CMAP signal 260 is supposed to vary smoothly from one phrenic nerve stimulation to the next one, even in the case of injury of the phrenic nerve. The palsy of the diaphragm indeed occurs progressively, such that the drop in CMAP amplitude also occurs progressively. A large deviation may thus be synonym with an artefact, and the monitoring unit may consider that the first occurrence of such a situation should be ignored, to avoid false positives, and thereby pausing the medical procedure undesirably. The deviation threshold may be larger than 15% and/or smaller than 25%, for example 20% (e.g., +/−2%).

As mentioned, the one or more monitoring electrodes may comprise more than two individual electrodes, and the monitoring unit may be configured for selectively operating the individual monitoring electrodes to form several (possible) dipoles therebetween. The monitoring unit may initially select (e.g., automatically) an optimal dipole among the one or more monitoring electrodes, for example during computation of the baseline value, and then operate the optimal dipole to capture and monitor the CMAP signal. In other words, after the optimal dipole is selected, the one or more monitoring electrodes are operated to form said optimal dipole (e.g., and any monitoring electrode not belonging to any of the two poles of the dipole is shut down), and the CMAP signal is captured exclusively by said dipole The optimal dipole may be one that optimizes one or several criteria, including for example a criterion that rewards a higher amplitude of the CMAP, a criterion that rewards a higher stability of the CMAP signal, and/or a criterion that penalizes presence of artefacts in the CMAP signal. The automatic selection of the optimal dipole may for example comprise optimizing an objective function which rewards a higher baseline amplitude of the CMAP (i.e., tending to select a dipole that provides the baseline CMAP highest in amplitude), rewards a higher baseline stability of the CMAP signal (i.e., tending to select a dipole that provides baseline the most stable CMAP signal), and/or penalizes presence of artefacts in the baseline CMAP signal (i.e., tending to select a dipole that provides a baseline CMAP signal with a minimal number of artefacts).

As mentioned, the apparatus may be configured to perform phrenic nerve stimulation and/or to be used in conjunction with another apparatus configured to perform phrenic nerve stimulation. The monitoring unit or a separate control unit may further be configured to command said phrenic nerve stimulation, for example by including a dedicated energy source.

In examples, the energy source may establish the electrical circuit by delivering electric pulses adapted for phrenic nerve stimulation. Each pulse may have a voltage above 1V and/or below 50V, for example between 2V and 25V, such as about 14V. Additionally or alternatively, each pulse may have a duration above 0.1 ms and/or below 20 ms, for example between 0.5 ms and 10 ms, such as about 2 ms. The period between two pairs of consecutive pulses may be constant or variable. In any case, said period may be below 20 s, 10 s or 5 s, and/or above 50 ms or 100 ms, for example between 100 ms and 10 s, such as about 1 s. Such period allows securely predicting an upcoming diaphragmatic palsy well-ahead of its occurrence, notably during a cardiac cryoablation procedure. Indeed, during a cardiac cryoablation procedure, it takes about 30 s between a decrease in diaphragmatic contraction response and the occurrence of the diaphragmatic palsy. The energy source may be configured to repeat delivering such pulses at least for a duration of a cardiac ablation procedure, for example at least for a duration of 120 s, such as at least for a duration between 180 s and 240 s. The energy source may be configured to iterate such repetition at least twice in a row (e.g., in less than ten minutes), corresponding to two cardiac ablation procedures each on a different right pulmonary vein of a same patient.

Figure 5:
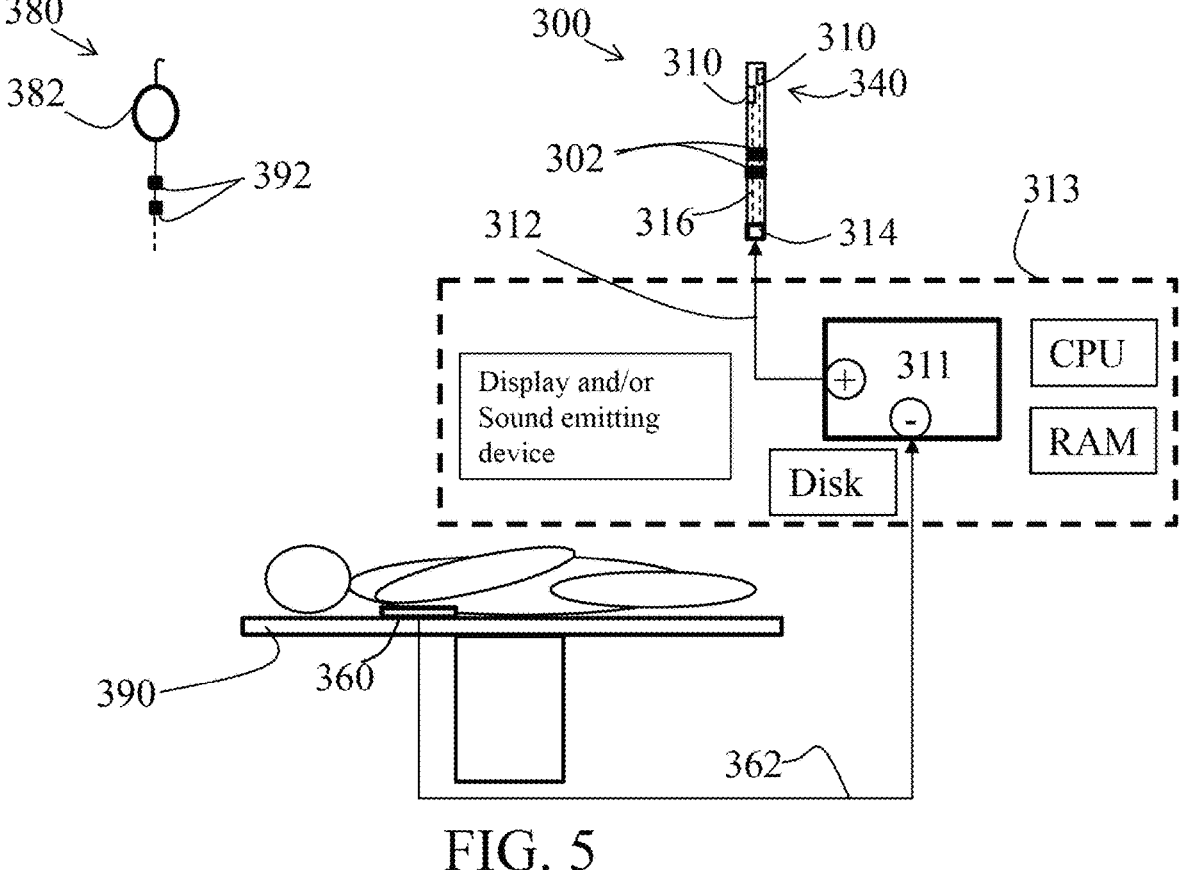
FIG. 5 shows an example of a cryoablation system comprising a stimulation and monitoring unit.

FIG. 5 shows an example of a cryoablation system comprising a stimulation and monitoring unit and used during a cardiac cryoablation method performed on a human patient, wherein the cryoablation method includes performing phrenic nerve stimulation repeatedly throughout the cryoablation procedure, and meanwhile, monitoring of the diaphragmatic activity. The discussion applies to any other type of ablation or atrial fibrillation ablation, such as electroporation or radiofrequency ablation by replacing the illustrated cryoballoon catheter 380 by an electroporation or radiofrequency ablation catheter.

The system comprises a stimulation catheter 300 including one or more intravascular stimulation electrodes 310 arranged on a distal portion 340 of the catheter, optionally an extracorporeal electrode patch 360, and optionally a monitoring and/or control unit 313 including an electricity interface 311. Electricity interface 311 is connectable to stimulation catheter 300 via an electrical cord 312 and an electrical connector 314 of stimulation catheter 300, so as to supply the stimulation electrodes 310 via electrical leads 316 respective to each intravascular electrode 310 (or alternatively, in case of several intravascular electrodes 310, a common single lead electrical). Electricity interface 311 is further connectable to patch 360 via an electrical cord 362. Thus, the monitoring and/or control unit 313 may be configured to operate patch 360 and intravascular stimulation electrode(s) 310 in a bipolar mode. Additionally or alternatively, the monitoring and/or control unit 313 may be configured to operate one or more pairs of intravascular stimulation electrodes 310 in a bipolar mode.

The unit 313 may optionally comprise a processor, such as a CPU, coupled to memory, such as non-volatile memory—e.g. hard disk—and/or RAM, and the processor may be configured for controlling the electricity interface 311, for example so as to deliver electric pulses that are configured for phrenic nerve stimulation, as earlier-described. For that, the memory may have recorded thereon a computer program comprising code instructions for operating the electricity interface 311.

The computer program may comprise instructions executable by the processor, the instructions comprising means for causing the above system to perform the electric pulse delivery of the stimulation method and/or the receiving and processing of an electrical signal captured by the one or more monitoring electrodes 302 to perform the diaphragmatic monitoring. The program may be recordable on any data storage medium. The program may for example be implemented in digital electronic circuitry, or in computer hardware, firmware, software, or in combinations of them. The program may be implemented as an apparatus, for example a product tangibly embodied in a machine-readable storage device for execution by a programmable processor. The application program may be implemented in a high-level procedural or object-oriented programming language, or in assembly or machine language if desired. In any case, the language may be a compiled or interpreted language. The program may be a full installation program or an update program.

The cryoablation method may comprise optionally affixing patch 360 to the human patient, laying the patient on his back over an operating table 390, introducing the stimulation catheter 300 in the superior vena cava of the patient, for example via a minimally invasive procedure.

The cryoablation method may further comprise providing a cryoablation catheter 380, such as a cryoballoon catheter, or any other type of ablation catheter. The cryoablation-catheter may be a cryogenic balloon catheter 380 having a balloon 382 for cryoablation. The cryoablation method further comprises introducing cryoballoon catheter 380 inside the left atrium of the patient's heart, for example via a minimally invasive procedure (e.g., through the femoral vein of the patient). The cryoablation method then comprises performing cryoablation (i.e., cold ablating body tissue), and meanwhile (i.e., substantially simultaneously), operating patch 360 and intravascular electrode(s) 310 in a bipolar mode with the unit 313 so as to repeatedly stimulate the patient's phrenic nerve, for example by delivering pulses of the order of 10V amplitude and of the order of a few ms duration, and at a frequency of the order of 60 pulses per minute (1 pulse/s).

The unit 313 may further be configured for monitoring a diaphragmatic response to phrenic nerve stimulation, for example via objective analysis, or the system may comprise a dedicated monitoring unit configured for that.

The stimulation catheter 300 comprises one or more monitoring electrodes 302 arranged on an intermediate portion of the catheter 300, so as to be positioned inside the inferior vena cava when the catheter 300 is introduced and operated inside the patient's vascular system. The one or more monitoring electrodes 302 are configured for capturing an electrical potential and to transmit said measurements to the unit 313, for example via respective electrical leads 316 and/or through electrical connector 314 and/or electrical interface 311. The unit 313 thereby receives a CMAP signal representing the diaphragmatic activity, and containing the diaphragmatic responses to each phrenic nerve stimulation signal. Additionally or alternatively, ablation catheter 380 may comprise one or monitoring electrodes 392 arranged on an intermediate portion of the catheter 380, so as to perform the same function. The one or monitoring electrodes 392 may provide a CMAP signal to unit 313 or another separate monitoring unit.

The unit 313 may further comprise any means to output a representation of the received measurements to the operator, such as a display (e.g., also configured to act as an alert generator), a sound emitting device acting as an alert generator (e.g., the alert may be visual and/or an audio cue), and/or a printer (for example adapted for transcription of the received measurements into a graph, e.g., printed on millimeter ECG paper). Thanks to such a monitoring unit, contraction of the diaphragmatic dome in response to the phrenic nerve stimulation may be monitored objectively, thus particularly accurately.

In case the response decreases, this means that an injury of the phrenic nerve is upcoming. The cryoablation method may comprise taking this into account. For example, the cryoablation may be paused, for instance upon or very soon after the observation of the response decrease (e.g., less than 20 s, 10 s, or 5 s after such observation). The cryoablation may be resumed only after observation that the response has retrieved its baseline state, meaning that the phrenic nerve has recovered. Thanks to the provided apparatus improving the monitoring of diaphragmatic activity, the cryoablation method is more secure with respect to phrenic injury and/or faster to perform since the monitored diaphragmatic response's reliability is improved.

Referring to FIGS. 6-10, different configuration examples of the apparatus are now discussed.

Figure 6:
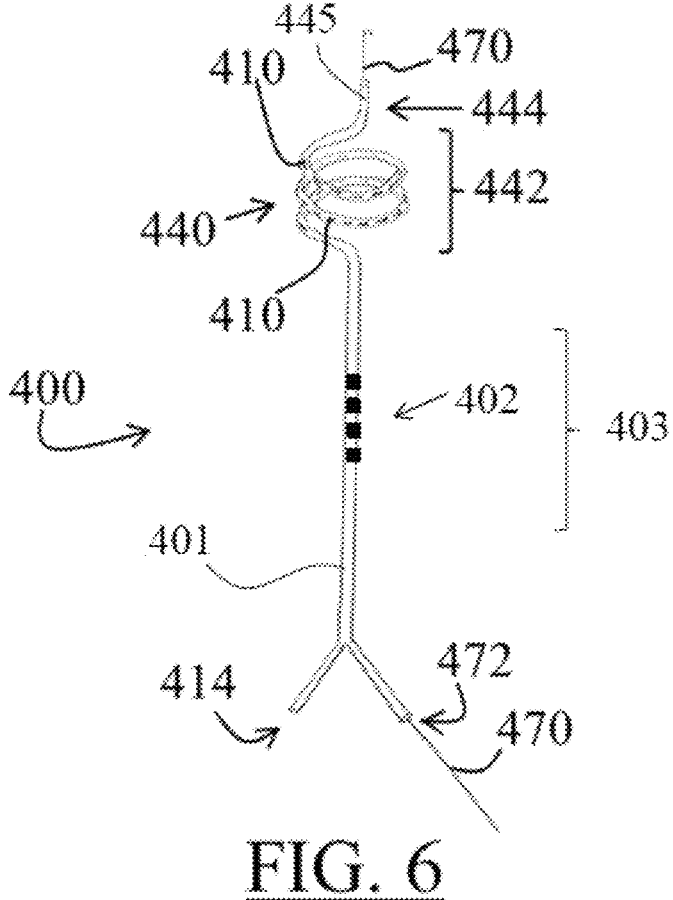
FIGS. 6-10 show different configuration examples of the apparatus of the disclosure.

FIG. 6 shows an example of the apparatus according to the first embodiment, comprising a catheter 400 that includes a distal portion 440 which is expandable in a helical configuration. The catheter 400 comprises one or more monitoring electrodes 402 on the intermediate portion 403 of catheter shaft 401, and configured for capturing electric signals when positioned in the inferior vena cava, so as to monitor the electrical activity of the diaphragm. The catheter 400 comprises an electrical connector 414 and a lumen entry 472. The lumen entry 472 may be configured, e.g., for introducing a guidewire 470. The guidewire 470 exits the extremity 444 of the distal portion. The guidewire 470 may be configured for the operator to position the distal portion 440 inside and/or beyond the superior vena cava region vessel, or at the ostium and/or inside a pulmonary vein. The electrical connector 414 may be connected to electrical leads. Each individual monitoring electrode 402 may have a respective electrical lead connecting the electrode 402 to the electrical connector 414, so as to enable transmission of electrical signals to a monitoring unit.

The distal portion comprises an expandable portion 442. The expandable portion may optionally comprise a plurality of intravascular stimulation or ablation electrodes 410 arranged circumferentially thereon. Alternatively, the expandable portion may comprise a single elongated stimulation or ablation electrode extending circumferentially along the expandable portion 442. The stimulation or ablation electrode or electrodes 410 may (e.g., individually or as a whole) have a respective electrical lead connecting the stimulation or ablation electrode or electrodes 410 to the electrical connector 414, so as to enable supplying of electricity to the stimulation or ablation electrode or electrodes 410 from the monitoring unit or from another control unit. The same catheter 400 can thus be used for delivering an energy in the heart region, for example for stimulating phrenic nerve in and/or beyond the right atrium, or for ablating tissue.

The expandable portion 442 may be adjusted or self-expanded, so that the intravascular electrodes 410 are positioned in an outward section of the walls of the expandable portion 442 to fit the wall of the vein. This provides stability to both the diaphragmatic monitoring and the energy delivery procedure. Optionally, the material of the extremity 444 may be made of a flexible material serving as a guide.

Optionally, the catheter 400 may comprise a straight distal end 445 which provides further stability to the apparatus.

Optionally, the catheter may comprise a retractable/withdrawable sheath (not shown) initially covering the expandable portion 442 (but sufficiently retractable to leave monitoring electrodes 402 uncovered) and/or a retractable inner straightening wire (not shown), that straightens the expandable portion to allow insertion of the catheter in the superior vena cava. Retraction of such sheath and/or inner straightening wire may allow expansion of the helix, and/or trigger said expansion. The principle presented on the figure applies to other types of expanded configuration. However, in such cases, the guidewire 470 may sometimes exit the catheter body, notably at the expandable portion, rather than always remain in a lumen formed in the catheter body as is the case on the figure. The catheter 400 may be used for both delivering an energy through the distal portion 440.

Figure 7:
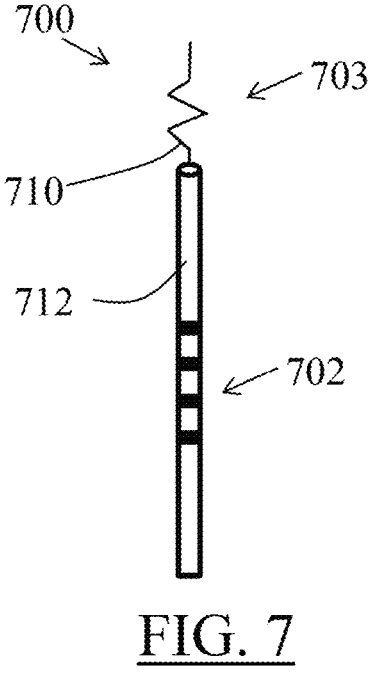

FIG. 7 shows schematically an example of the apparatus according to the first embodiment, where the apparatus 700 comprises a catheter 710 having a (e.g., expandable and/or helical) distal portion 703. The apparatus 700 further comprises a catheter sheath 712. The catheter sheath 712 is partly retractable, so as to allow operation and optionally expansion of the distal portion 703. The catheter sheath 712 comprises one or more monitoring electrodes 702 arranged on an intermediate portion of the sheath 712, so as to be positioned inside the inferior vena cava when the apparatus 700 is at the operating location, preferably beneath the right diaphragmatic dome for at least two electrodes 702 operated as a dipole. The one or more monitoring electrodes 702 are configured for capturing electric signals when positioned in the inferior vena cava, so as to monitor the electrical activity of the diaphragm.

Figure 8:
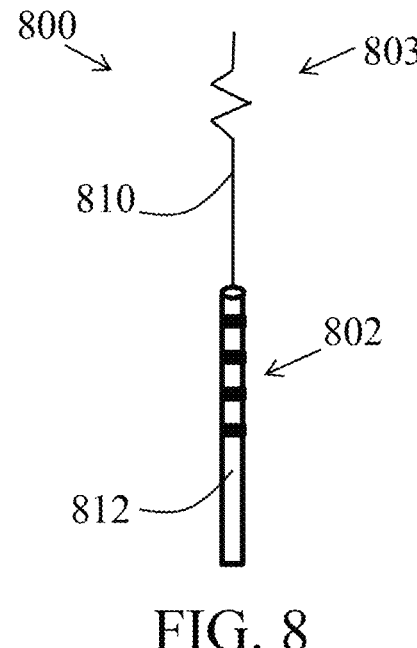

FIG. 8 shows schematically an example of the apparatus according to the first embodiment, where the apparatus 800 comprises a catheter 810 having a (e.g., expandable and/or helical) distal portion 803. The apparatus 800 further comprises a catheter sheath 812. The catheter sheath 812 is partly retractable, so as to allow operation and optionally expansion of the distal portion 803. The apparatus 800 differs from the apparatus 700 of FIG. 7 in that the catheter sheath 812 is to be retracted at a larger extent. The catheter sheath 812 also comprises one or more monitoring electrodes 802, but arranged on a distal portion of the sheath 812, so as to be positioned inside the inferior vena cava when the apparatus 800 is at the operating location, preferably beneath the right diaphragmatic dome for at least two electrodes 802 operated as a dipole. The one or more monitoring electrodes 802 are configured for capturing electric signals when positioned in the inferior vena cava, so as to monitor the electrical activity of the diaphragm.

Figure 9:
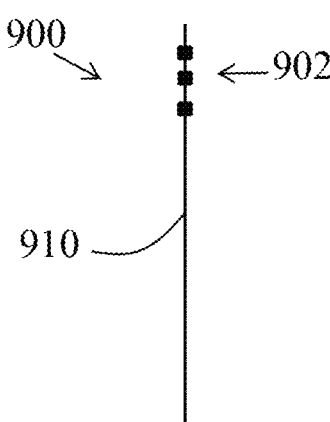

FIG. 9 shows schematically an example of the apparatus according to the second embodiment, where apparatus 900 comprises a catheter 910 which comprises one or more monitoring electrodes 902 on a distal portion of catheter 910. The catheter 910 can be positioned such that the one or more monitoring electrodes 902 are positioned inside the inferior vena cava when the apparatus 900 is at the operating location, preferably beneath the right diaphragmatic dome for at least two electrodes 902 operated as a dipole. The one or more monitoring electrodes 902 are configured for capturing electric signals when positioned in the inferior vena cava, so as to monitor the electrical activity of the diaphragm.

Figure 10:
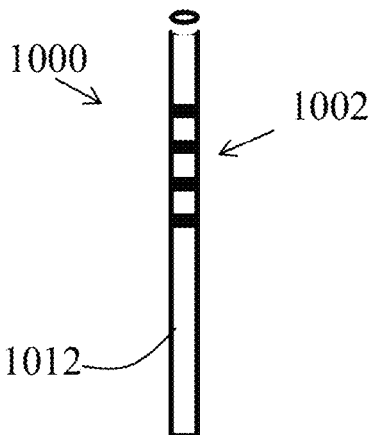

FIG. 10 shows schematically an example of the apparatus according to the second embodiment, where apparatus 1000 comprises a catheter sheath 1012 which comprises one or more monitoring electrodes 1002 on a distal portion of catheter sheath 1012. The catheter sheath 1012 can be used in conjunction with a separate catheter, and positioned such that the one or more monitoring electrodes 1002 are positioned inside the inferior vena cava when the apparatus 1000 is at the operating location, preferably beneath the right diaphragmatic dome for at least two electrodes 1002 operated as a dipole. The one or more monitoring electrodes 1002 are configured for capturing electric signals when positioned in the inferior vena cava, so as to monitor the electrical activity of the diaphragm.

Figure 11:
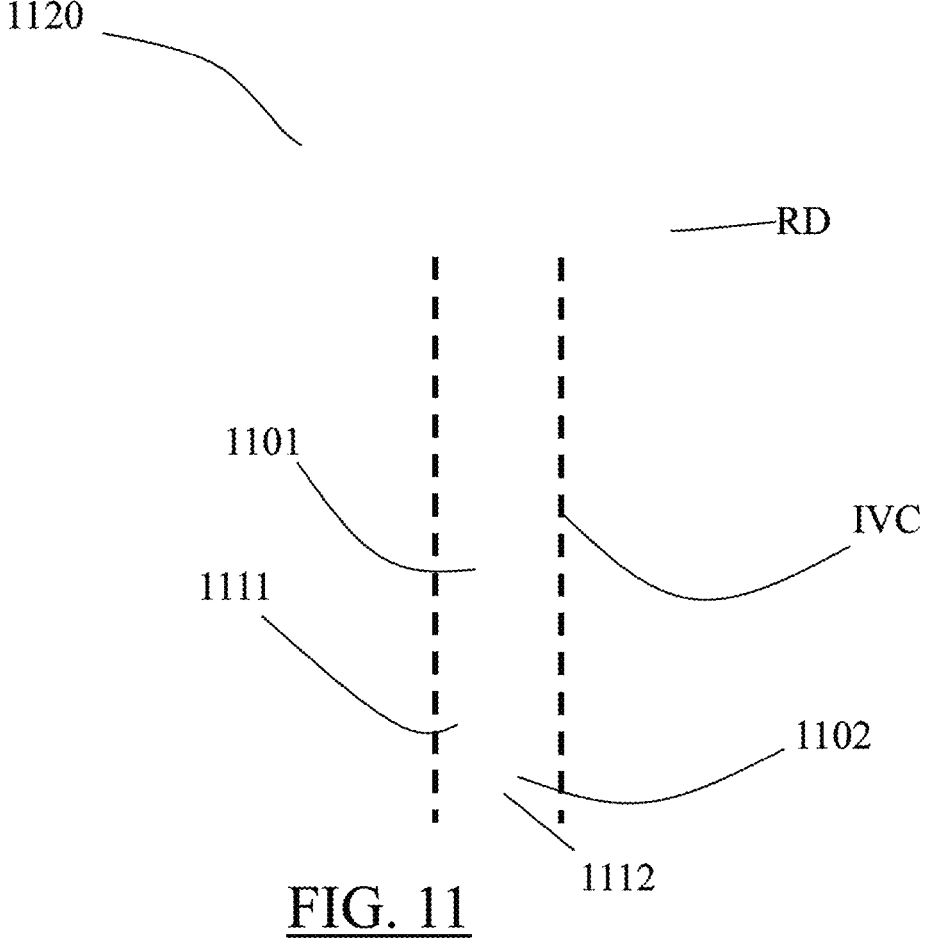
FIGS. 11-12 illustrate an experiment that was conducted to validate the proposed approach.
Figure 12:
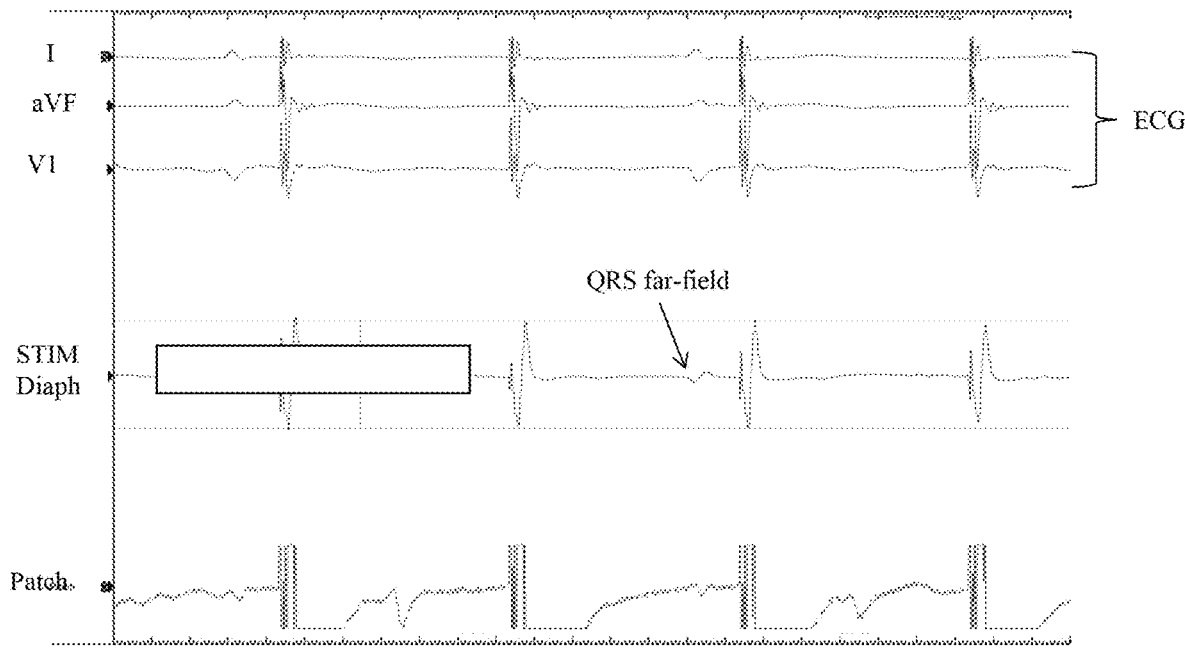

Referring to FIGS. 11-12, an experiment that was conducted to validate the proposed approach is now discussed.

FIG. 11 shows an echography of a patient's thorax, on which the experiment was conducted. A first catheter 1111 having a monitoring electrode 1101 and a second catheter 1112 having a monitoring electrode 1102 were both introduced inside the patient's inferior vena cava IVC, so as to position the two monitoring electrodes 1101 and 1102 beneath the right diaphragmatic dome RD, at different vertical positions. The two monitoring electrodes 1101 and 1102 were then operated as a dipole to capture the CMAP signal representing electrical activity the diaphragm. Two separate catheters were used in the experiment, but the recorded signal would be similar in case of a dipole formed by two monitoring electrodes on a same catheter shaft. A skin patch electrode 1120 was also used to recorded a CMAP for control.

FIG. 12 shows the results that were obtained, were the CMAP signal recorded by the two monitoring electrodes 1101 and 1102 is denoted "STIM Diaph", as in "stimulation diaphragmatic response". As can be seen, the CMAP signal that was obtained is a very clean sharp and biphasic signal, with no 50 Hz artifact, with a limited or no interference created by the stimulation or pacing artefact, and with limited interference created by the QRS far-field (even if it was concomitant with the CMAP pattern). In contrast, the signal obtained by the skin electrode and denoted "Patch" on the figure is much noisier, and perturbated or easy to perturbate by the above-mentioned artefacts and QRS far-field.

The invention claimed is:

1. A method of minimally invasive medical use of an apparatus comprising an elongated part including a catheter and/or a catheter sheath, the elongated part having a distal portion and an intermediate portion, the intermediate portion being located proximally relative to the distal portion, one or more monitoring electrodes being arranged on the intermediate portion of the elongated part, the method comprising:

introducing the elongated part inside an inferior vena cava of a human patient, and positioning the elongated part at an operating location where the distal portion is in and/or beyond a right atrium and, at a same time, the intermediate portion is in the inferior vena cava;

while the elongated part is at the operating location and the one or more monitoring electrodes are thereby located in the inferior vena cava, and while at the same time the distal portion is located in and/or beyond the right atrium, performing a phrenic nerve stimulation of the human patient, and by the one or more monitoring electrodes, capturing an electrical signal representing an electrical activity of a diaphragm of the human patient; and monitoring the electrical activity of the diaphragm of the human in response to the phrenic nerve stimulation.

2. The method of claim 1, wherein the method further comprises performing a stimulation of a right phrenic nerve of the patient, while performing the monitoring of the electrical activity of the diaphragm of the human patient.

3. The method of claim 2, wherein the method further comprises detecting a time when a diaphragmatic response to the phrenic nerve stimulation indicates a current or upcoming diaphragmatic palsy.

4. The method of claim 3, wherein the method further comprises, upon detection of the time when the diaphragmatic response to the phrenic nerve stimulation indicates a current or upcoming diaphragmatic palsy, outputting an alert.

5. The method of claim 1, wherein the method further comprises performing cardiac tissue ablation.

6. The method of claim 1, wherein the elongated part includes the catheter, the distal portion includes an extremal portion of the catheter, and the extremal portion comprises an energy measurement and/or delivery tool.

7. The method of claim 6, wherein the energy measurement and/or delivery tool comprises one or more electrodes, one or more probes, and/or one or more cryotherapy delivery tools.

8. The method of claim 6, wherein the energy measurement and/or delivery tool comprises one or more stimulation electrodes, the method comprising introducing the catheter in a superior vena cava of the human patient so as to position the one or more stimulation electrodes in the superior vena cava, in a right brachiocephalic vein, and/or in a right subclavian vein, the method being performed with the one or more stimulation electrodes for stimulation of a right phrenic nerve.

9. The method of claim 1, wherein the one or more monitoring electrodes comprise at least one monitoring electrode arranged on an external surface of the intermediate portion.

10. The method of claim 1, wherein the elongated part includes the catheter sheath, and the one or more monitoring electrodes comprise at least one monitoring electrode arranged on the catheter sheath.

11. The method of claim 1, wherein the elongated part includes the catheter, the catheter is a sheath-less catheter or a withdrawable-sheath catheter, the catheter has a shaft, and the one or more monitoring electrodes comprise at least one monitoring electrode arranged on the shaft.

12. The method of claim 1, wherein the one or more monitoring electrodes comprise at least two electrodes arranged at different longitudinal positions of the intermediate portion.

13. The method of claim 12, wherein the at least two electrodes comprise a first electrode at a distance from a second electrode higher than or equal to 1 cm and/or lower than or equal to 20 cm, for example between 5 cm and 10 cm.

14. The method of claim 1, wherein the elongated part has a distal end, and the one or more monitoring electrodes comprise at least one electrode arranged, when the elongated part is positioned at the operating location, at a distance from the distal end higher than or equal to 10 cm and/or lower than or equal to 50 cm, for example between 15 cm and 30 cm.

15. The method of claim 1, wherein the one or more monitoring electrodes comprises at least two individual electrodes configured to form a dipole.

* * * * *